(12) United States Patent
Imanishi et al.

(10) Patent No.: US 8,467,055 B2
(45) Date of Patent: Jun. 18, 2013

(54) OPTICAL MEASURING DEVICE

(75) Inventors: Shingo Imanishi, Kanagawa (JP); Takeo Arai, Saitama (JP); Suguro Dowaki, Kanagawa (JP)

(73) Assignee: Sony Corporation, Tokyo (JP)

( * ) Notice: Subject to any disclaimer, the term of this patent is extended or adjusted under 35 U.S.C. 154(b) by 525 days.

(21) Appl. No.: 12/579,754

(22) Filed: Oct. 15, 2009

(65) Prior Publication Data

US 2010/0096560 A1 Apr. 22, 2010

(30) Foreign Application Priority Data

Oct. 16, 2008 (JP) .............................. P2008-267202
Aug. 21, 2009 (JP) .............................. P2009-192617

(51) Int. Cl.
*G01N 21/00* (2006.01)

(52) U.S. Cl.
USPC ......................................... 356/344; 356/317

(58) Field of Classification Search
USPC ................. 356/344, 317, 318, 417, 300, 311, 356/402, 416; 250/458.1, 208.2, 459.1, 200, 250/206
See application file for complete search history.

(56) References Cited

U.S. PATENT DOCUMENTS

| 5,062,942 | A | * | 11/1991 | Kambara et al. | 204/612 |
| 5,491,344 | A | * | 2/1996 | Kenny et al. | 250/461.1 |
| 7,239,384 | B2 | * | 7/2007 | Kawano | 356/317 |
| 7,280,204 | B2 | | 10/2007 | Robinson et al. | |
| 2007/0154938 | A1 | * | 7/2007 | Oshida et al. | 435/6 |
| 2008/0316482 | A1 | | 12/2008 | Hoshizaki et al. | |

FOREIGN PATENT DOCUMENTS

| JP | 61-173141 | 8/1986 |
| JP | SHO 61-173141 | 8/1986 |
| JP | 5-10946 | 1/1993 |
| JP | 2001-108684 | 4/2001 |
| JP | 2005-208573 | 8/2005 |
| JP | 2006-153763 | 6/2006 |
| JP | 2006-251732 | 9/2006 |
| JP | 2007-101824 | 4/2007 |
| JP | 2007-240228 | 9/2007 |
| JP | 2008-519266 | 6/2008 |
| WO | 2006/052682 A2 | 5/2006 |
| WO | 2007/094782 A1 | 8/2007 |
| WO | 2008 054558 A2 | 5/2008 |

* cited by examiner

Primary Examiner — Tri T Ton
(74) Attorney, Agent, or Firm — K&L Gates LLP

(57) ABSTRACT

An optical measuring device includes: a light applying section configured to apply laser light to a sample flowing in a channel; and a fluorescence detecting section configured to detect fluorescence generated from the sample irradiated with the laser light; the fluorescence detecting section including a multichannel photomultiplier tube having a plurality of detection channels capable of simultaneously detecting a plurality of light beams, a light separator configured to separate the fluorescence according to wavelengths to provide the plurality of light beams, the light separator being provided by a transmission grating or a prism, and a telecentric condenser lens configured to receive the plurality of light beams from the light separator and direct the plurality of light beams toward the plurality of detection channels of the multichannel photomultiplier tube so that the optical axes of the plurality of light beams are parallel to each other.

12 Claims, 15 Drawing Sheets

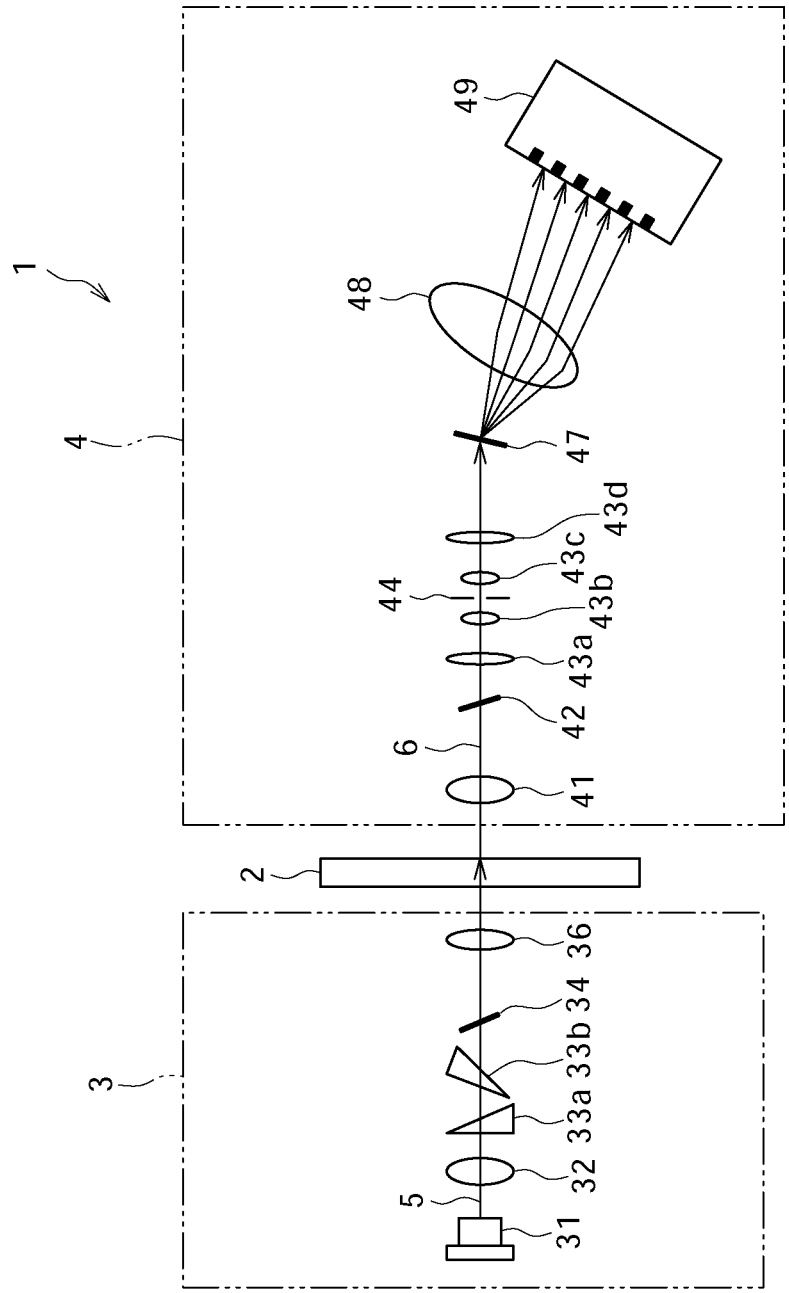

F I G. 4 A
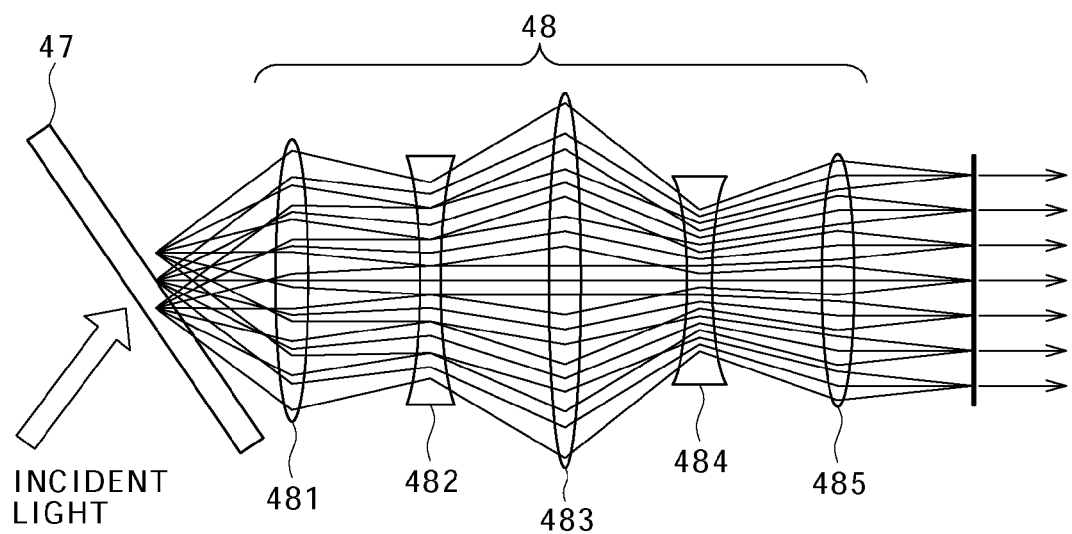
F I G. 4 B
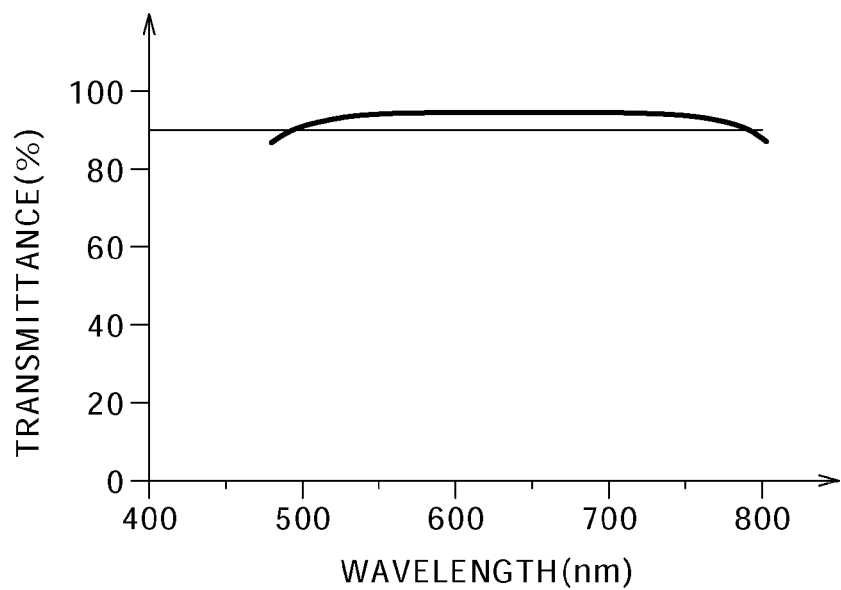

F I G . 9
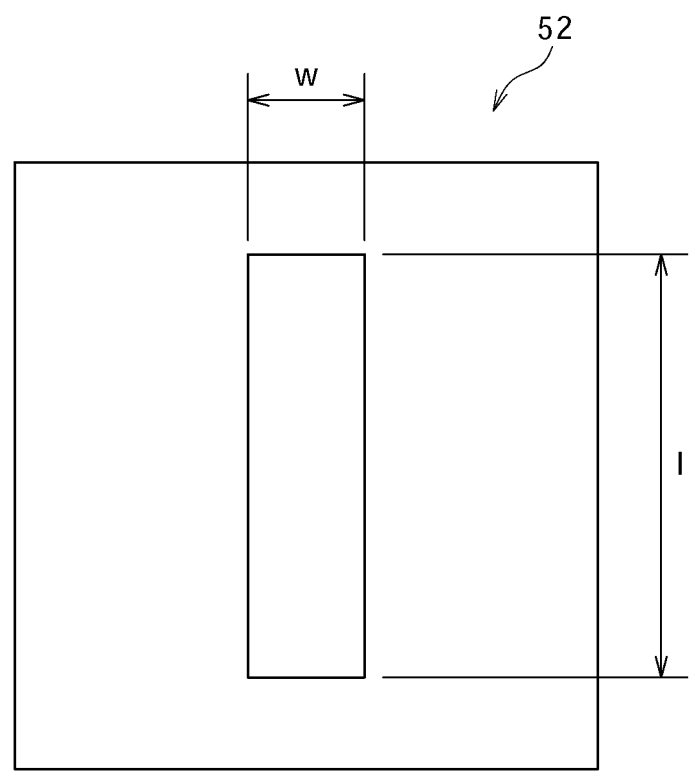

OPTICAL MEASURING DEVICE

CROSS REFERENCES TO RELATED APPLICATIONS

The present application claims priority to Japanese Priority Patent Application JP 2009-192617 filed in the Japan Patent Office on Aug. 21, 2009, which claims priority to Japanese Priority Patent Application JP 2008-267202 filed in Japan Patent Office on Oct. 16, 2008 the entire content of which is hereby incorporated by reference.

BACKGROUND

The present application relates to an optical measuring device for identifying a sample such as minute particles flowing in a channel, and more particularly to a technique for identifying the kind etc. of the sample by detecting fluorescence generated from the sample irradiated with laser light having a specific wavelength.

In the case of identifying biological minute particles such as cells, microorganisms, and ribosomes, an optical measuring method using flow cytometry (flow cytometer) is generally used (see Hiromitsu Nakauchi, supervisor, "Cell Engineering Separate Volume, Experimental Protocol Series, Flow Cytometry Jiyujizai," Second Ed., Shujunsha Co., Ltd (Aug. 31, 2006), for example). The flow cytometry is a method of individually identifying a plurality of minute particles flowing in a line in a channel by applying laser light having a specific wavelength to the minute particles and detecting fluorescence or scattered light generated from each minute particle irradiated with the laser light.

More specifically, a sample liquid containing a plurality of minute particles as an object to be measured and a sheath liquid flowing around the sample liquid form a laminar flow in a flow cell to line the minute particles contained in the sample liquid. In this condition, laser light is applied to the flow cell, so that the minute particles are individually passed through the laser beam. At this time, each minute particle is excited by the laser light to generate fluorescence and/or scattered light, which are/is next detected by using a photodetector such as a CCD (Charge Coupled Device) or a PMT (Photo-Multiplier Tube). The light detected by the photodetector is converted into an electrical signal and digitized to perform statistical analysis, thereby determining the kind, size, structure, etc. of each minute particle.

In related art, proposed is a flow cytometer using a multichannel photodetector having a plurality of detection channels, such as a multianode photomultiplier tube (see U.S. Pat. No. 7,280,204 (hereinafter referred to as Patent Document 1) and Japanese Patent Laid-open No. Hei 5-10946 (hereinafter referred to as Patent Document 2), for example). Such an existing flow cytometer using a multichannel photodetector as described in Patent Documents 1 and 2 can simultaneously measure a plurality of light beams having different wavelengths. In the device described in Patent Document 2, a multianode photomultiplier tube is used as a photodetector to detect light intensity at each detection channel by counting photons, thereby improving the detectivity and reproducibility.

SUMMARY

However, the existing flow cytometer using a multichannel photodetector as described in Patent Documents 1 and 2 has the following problems. In recent years, a multichannel photomultiplier tube such as a 32-channel photomultiplier tube has been developed. By using such a multichannel photomultiplier tube as a detector, more kinds of coloring matter can be simultaneously detected. However, when such a multichannel photomultiplier tube is used as a detector, the number of photons detectable per channel is reduced to cause a reduction in detectivity.

In the case of using a chip having a plastic substrate formed with a channel in place of the flow cell for the measurement, fluorescence is also generated from the plastic substrate constituting the chip, so that a noise component is increased to cause a reduction in detection accuracy. Such a disturbance component generated from any matter other than the sample can be removed by providing a pinhole in an optical path. However, when the diameter of the pinhole is small, the detectivity is reduced, whereas when the diameter of the pinhole is large, the noise component is increased.

Further, in an optical measuring device such as a flow cytometer, various optical components such as a diffraction grating, a beam splitter, and a condenser lens are provided to separate the fluorescence generated from the sample according to specific wavelengths, causing an increase in size of the device.

It is desirable to provide an optical measuring device which can detect fluorescence generated from a sample with high sensitivity and can be made compact although a multichannel photomultiplier tube is used as a detector.

In accordance with a present embodiment, there is provided an optical measuring device including a light applying section configured to apply laser light to a sample flowing in a channel; and a fluorescence detecting section configured to detect fluorescence generated from the sample irradiated with the laser light; the fluorescence detecting section including at least a multichannel photomultiplier tube having a plurality of detection channels capable of simultaneously detecting a plurality of light beams; a light separator configured to separate the fluorescence according to wavelengths to provide the plurality of light beams, the light separator being provided by a transmission grating or a prism; and a telecentric condenser lens configured to receive the plurality of light beams from the light separator and direct the plurality of light beams toward the plurality of detection channels of the multichannel photomultiplier tube so that the optical axes of the plurality of light beams are parallel to each other.

In the optical measuring device according to a present embodiment, the fluorescence is separated by the transmission grating or a prism. Accordingly, loss of the fluorescence can be reduced and the space for installation of the transmission grating can be saved as compared with an existing reflection grating. Further, the light beams separated by the transmission grating or the prism are condensed to the detection channels of the multichannel photomultiplier tube by the telecentric condenser lens. Accordingly, although the multichannel photomultiplier tube is used as a detector, the fluorescence generated from the sample can be detected with high sensitivity.

Preferably, the telecentric condenser lens is configured by combining a plurality of lenses different in characteristics, and has a transmittance of 90% or more to the light having a wavelength range of at least 500 to 800 nm. In this case, loss of the fluorescence can be greatly reduced and the focal position can be set at a short distance from the telecentric condenser lens.

In the case that the light separator is provided by the prism, the telecentric condenser lens preferably includes an aspherical lens.

Preferably, the light separator includes at least one prism having a positive temperature coefficient of refractive index and at least one prism having a negative temperature coefficient of refractive index.

Preferably, the fluorescence detecting section further includes a microlens array provided between the telecentric condenser lens and the multichannel photomultiplier tube; and the plurality of light beams emerged from the telecentric condenser lens are passed through the microlens array to enter the plurality of detection channels of the multichannel photomultiplier tube.

In this case, preferably, the microlens array is composed of a plurality of cylindrical lens arranged so that the axes of the cylindrical lenses are parallel to each other, the number of the cylindrical lenses corresponding to the number of the detection channels of the multichannel photomultiplier tube; and the direction of arrangement of the cylindrical lens coincides with the direction of arrangement of the detection channels of the multichannel photomultiplier tube.

Preferably, the fluorescence detecting section further includes an objective lens configured to condense the fluorescence generated from the sample; and the objective lens is configured by combining a plurality of lenses different in characteristics, and has a focal length of 8 mm or more, a numerical aperture NA of 0.8 or more, and a field diameter of 150 μm or more.

In this case, preferably, the fluorescence detecting section further includes a rectangular slit provided between the objective lens and the light separator, the rectangular slit having a length of 0.2 to 1.5 mm and a width of 0.4 mm or less; and the slit is arranged so that the longitudinal direction of the slit is parallel to the flowing direction of the sample or a pinhole is arranged.

In this case, preferably, the fluorescence detecting section further includes a polarization beam splitter and a Fresnel rhomb provided between the objective lens and the light separator; the polarization beam splitter being capable of separating the light having a wavelength range of at least 500 to 800 nm into a parallel polarized light component and an orthogonal polarized light component; the Fresnel rhomb being capable of 90° rotating the polarization direction of one of the parallel polarized light component and the orthogonal polarized light component separated by the polarization beam splitter.

According to the present embodiment, the light beams separated by the transmission grating or the prism are condensed to the detection channels of the multichannel photomultiplier tube by the telecentric condenser lens. Accordingly, although the multichannel photomultiplier tube is used as a detector, the fluorescence generated from the sample can be detected with high sensitivity. Further, since the focal position can be set at a short distance from the telecentric condenser lens, the device can be made compact.

Additional features and advantages are described herein, and will be apparent from the following Detailed Description and the figures.

BRIEF DESCRIPTION OF THE FIGURES

FIG. 1 is a schematic diagram showing the configuration of an optical measuring device according to a first embodiment;

FIG. 4A is a schematic diagram showing the configuration of a telecentric condenser lens;

FIG. 4B is a graph showing the relation between wavelength and transmittance in the telecentric condenser lens shown in FIG. 4A, wherein the horizontal axis represents wavelength and the vertical axis represents transmittance;

FIG. 9 is a plan view schematically showing the configuration of a slit used in the optical measuring device shown in FIG. 8;

DETAILED DESCRIPTION

Figure 2A:
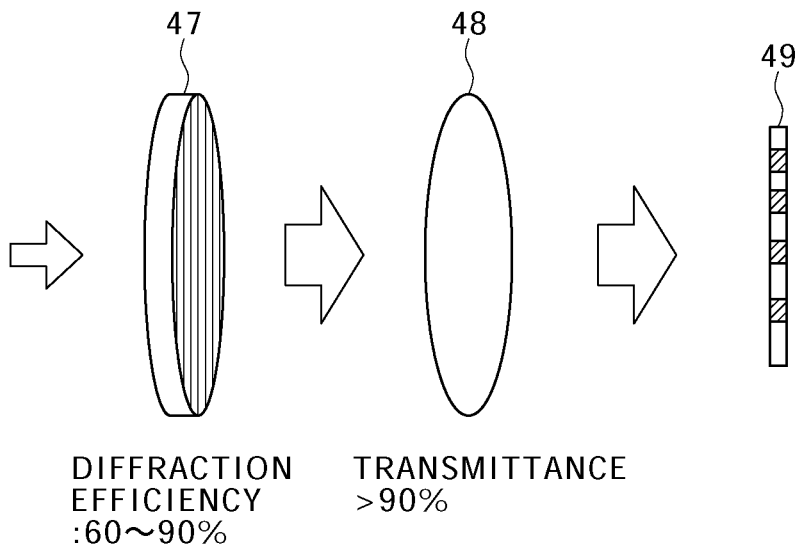
FIG. 2A is a schematic diagram showing the location and efficiency of each optical component in a fluorescence detecting section of the optical measuring device shown in FIG. 1.

The present application will be described in detail with reference to the attached drawings according to the embodiment.

General Configuration of the Optical Measuring Device

FIG. 1 is a schematic diagram showing the configuration of an optical measuring device 1 according to a first embodiment. As shown in FIG. 1, the optical measuring device 1 includes a light applying section 3 for applying laser light 5 to a sample flowing in a channel and a fluorescence detecting section 4 for detecting fluorescence 6 generated from the sample irradiated with the laser light 5. The optical measuring device 1 uses a chip having an internal minute channel (which will be hereinafter referred to as a channel chip 2).

Configuration of the Light Applying Section 3

The light applying section 3 in the optical measuring device 1 includes a laser light source 31, a condenser lens 32, anamorphic lenses 33a and 33b, a bandpass filter 34, and an objective lens 36, which are arranged in this order in the traveling direction of the laser beam 5. The bandpass filter 34 is an optical filter having characteristics such that it transmits only light having a specific wavelength and reflects light having the other wavelengths. By providing such a filter, unwanted light components can be removed.

Examples of the laser light source 31 may include a laser diode, SHG (Second Harmonic Generation) laser, gas laser, and high-luminance LED (Light Emitting Diode). However, the laser light source 31 is not limited to these examples in the present application, but any other examples may be suitably selected according to measurement content or the like. As a modification, a plurality of light sources capable of generating light having different wavelengths may be provided in the light applying section 3. The light applying section 3 essentially has a configuration such that it can apply light having a specific wavelength to a sample flowing in the channel of the channel chip 2. Further, the kind and location of various optical components such as a light source, lenses, and optical filter in the light applying section may be suitably selected and is not limited to the configuration described above.

Configuration of the Fluorescence Detecting Section 4

The fluorescence detecting section 4 in the optical measuring device 1 essentially includes a multichannel PMT (Photo-Multiplier Tube) 49 such as a 32-channel PMT, a transmission grating 47, and a telecentric condenser lens 48. The fluorescence detecting section 4 may further include an objective lens 41 for condensing the fluorescence 6 generated from the sample and a pinhole 44 for removing a disturbance component generated from any matter other than the sample. Further, as demanded, the fluorescence detecting section 4 may still further include a band-cut filter 42 provided between the objective lens 41 and the pinhole 44 for reflecting light having a specific wavelength, condenser lenses 43a and 43b provided between the band-cut filter 42 and the pinhole 44, and condenser lenses 43c and 43d provided between the pinhole 44 and the transmission grating 47.

(Multichannel PMT 49)

The multichannel PMT 49 provided in the fluorescence detecting section 4 is a detector for detecting the fluorescence 6 generated from the sample. This detector has a plurality of detection channels capable of simultaneously detecting a plurality of light beams. Such a PMT has such a configuration that photons enter each detection channel from its incidence window and the photons are converted into photoelectrons on a photoelectric surface and that the photoelectrons are amplified and output as an electrical signal. Accordingly, if the quantum efficiency of the photoelectric surface of the multichannel PMT 49 is low, there is a problem such that the spread of a Poisson distribution of an output cannot be suppressed in spite of an increase in number of photons entering each detection channel. It is therefore preferable to improve the quantum efficiency of the photoelectric surface of the multichannel PMT 49. As a result, a larger signal quantity can be obtained to thereby improve the detectivity of the PMT. More specifically, in the case that light having a wavelength of 490 nm is applied and the maximum quantum efficiency of the photoelectric surface is improved from 18% to 25%, the detectivity of the PMT can be improved by one and a half times.

Transmission Grating 47

Figure 2B:
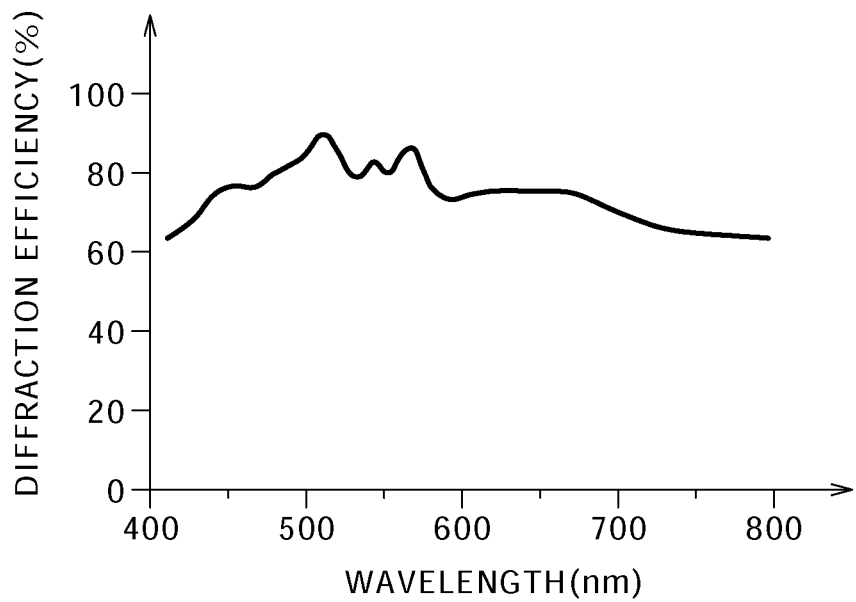
FIG. 2B is a graph showing the relation between wavelength and diffraction efficiency in the case of using a transmission grating, wherein the horizontal axis represents wavelength and the vertical axis represents diffraction efficiency.
Figure 3A:
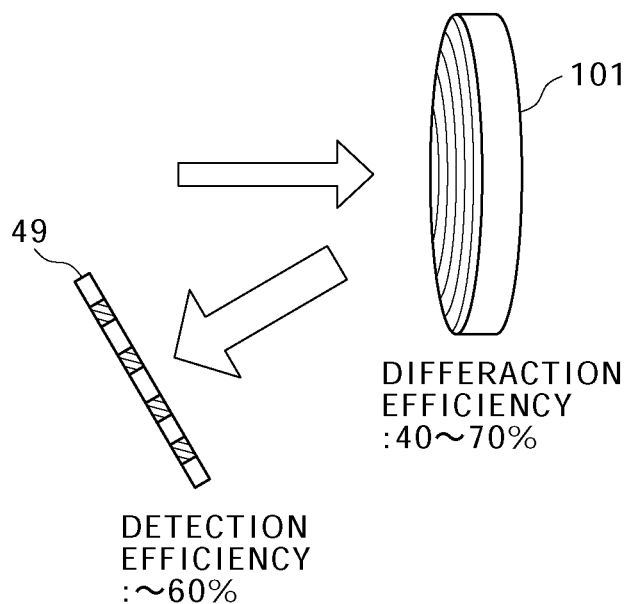
FIG. 3A is a schematic diagram showing the configuration of a detecting section using a reflection grating in an existing device.

The transmission grating 47 is a light separator for separating the fluorescence 6 generated from the sample into wavelength components. FIG. 2A is a schematic diagram showing the location and efficiency of each optical component in the fluorescence detecting section 4 shown in FIG. 1, and FIG. 2B is a graph showing the relation between wavelength and diffraction efficiency in the case of using the transmission grating 47, wherein the horizontal axis represents wavelength and the vertical axis represents diffraction efficiency. FIG. 3A is a schematic diagram showing the configuration of a detecting section using a reflection grating 101 in an existing device, and FIG. 3B is a graph showing the relation between wavelength and diffraction efficiency in the case of using the reflection grating 101, wherein the horizontal axis represents wavelength and the vertical axis represents diffraction efficiency.

The multichannel PMT 49 has a dead zone between any adjacent ones of the detection channels, wherein the dead zone does not detect light. In the case that the diffracted light from the reflection grating 101 is directly incident on the multichannel PMT 49 as shown in FIG. 3A, it is difficult to efficiently condense the incident light on each detection channel as avoiding each dead zone, causing a reduction in detection efficiency. Further, when an optical component such as a lens is provided to efficiently condense the incident light on each detection channel, an installation space for the optical component is demanded, so that the device becomes large in size.

To the contrary, the optical measuring device 1 according to this embodiment uses the transmission grating 47 as shown in FIG. 2A. Accordingly, the installation space for the transmission grating 47 can be reduced as compared with that for the reflection grating 101. As a result, it is possible to ensure a space for installing a condensing optical system between the transmission grating 47 and the multichannel PMT 49.

Figure 3B:
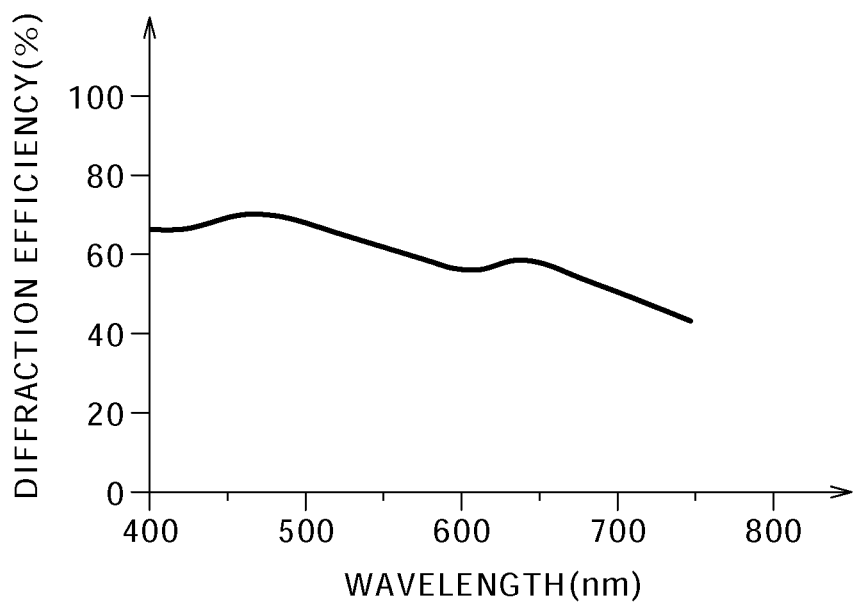
FIG. 3B is a graph showing the relation between wavelength and diffraction efficiency in the case of using the reflection grating, wherein the horizontal axis represents wavelength and the vertical axis represents diffraction efficiency.

In the case that the transmission grating 47 has a rectangular groove structure, a diffraction efficiency greater than or equal to that of the reflection grating 101 can be attained in a wavelength range of 400 to 800 nm as shown in FIGS. 2B and 3B. It is sufficient that the diffraction efficiency of the transmission grating 47 be greater than or equal to that of the reflection grating 101 in a wavelength range of at least 500 to 800 nm. Although the fluorescence detecting section 4 uses the multichannel PMT 49, the improvement in detection efficiency and the space saving in the fluorescence detecting section 4 can be realized by using the transmission grating 47.

Telecentric Condenser Lens 48

The telecentric condenser lens 48 is an optical component for making parallel the optical axes of the plural light beams (diffracted light) separated by the transmission grating 47 and directing these parallel light beams toward the plural detection channels of the multichannel PMT 49. The telecentric condenser lens 48 is provided between the transmission grating 47 and the multichannel PMT 49, so that the separated light beams from the transmission grating 47 can be efficiently condensed toward the plural detection channels of the multichannel PMT 49 without providing a plurality of optical components.

Preferably, the telecentric condenser lens 48 has a transmittance of 90% or more to the light having a wavelength range of at least 500 to 800 nm. Accordingly, optical loss in the telecentric condenser lens 48 can be suppressed to improve the detection efficiency in the multichannel PMT 49. The telecentric condenser lens 48 may be realized by combining a plurality of lenses having different characteristics.

FIG. 4A is a schematic diagram showing the configuration of the telecentric condenser lens 48 by way of example, and FIG. 4B is a graph showing the relation between wavelength and transmittance in the telecentric condenser lens 48 shown in FIG. 4A, wherein the horizontal axis represents wavelength and the vertical axis represents transmittance. More specifically, in the case that the telecentric condenser lens 48 is composed of a plurality of lenses 481 to 485 different in shape and characteristics as shown in FIG. 4A, the transmittance of the telecentric condenser lens 48 to the light having a wavelength range of 500 to 800 nm can be set to 90% or more as shown in FIG. 4B.

In the case that each lens constituting the telecentric condenser lens 48 is provided by a lens formed of a glass material having a large refractive index and a large Abbe number, a degradation in aberration can be suppressed and the transmittance can be greatly improved. Examples of such a glass material may include SLAH60 and SNPH2. Further, an AR (Anti-Reflection) coating of multiple layers is preferably formed on the surface of each lens. Accordingly, the reflectance of each lens can be reduced. Preferably, the telecentric condenser lens 48 used in the optical measuring device 1 has a reflectance of 0.2 to 0.8% to at least the light having a wavelength range of 500 to 800 nm. Such an AR coating may be formed by alternately layering two kinds of dielectric films each having a predetermined thickness, wherein these two kinds of dielectric films have high transmittances to the light having the above wavelength range and different refractive indices.

Objective Lens 41

The objective lens 41 provided in the fluorescence detecting section 4 may be configured by combining a plurality of lenses having different characteristics. Preferably, the objective lens 41 has a focal length of 8 mm or more, a numerical aperture NA of 0.8 or more, and a field diameter of 150 μm or more. If the numerical aperature NA of the objective lens 41 is low, the number of photons that can be trapped is reduced. Since a signal output spreads according to a Poisson distribution due to quantization error, an S/N in the multichannel PMT 49 is reduced.

To cope with this problem, the objective lens 41 used in the optical measuring device 1 according to this embodiment has a large focal length to widen the field diameter. Thus, the fluorescence 6 is trapped by the objective lens 41 having a wide field and a high numerical aperture, so that the fluorescence generated from the sample flowing in the channel can be detected with high efficiency for a long time period, thereby increasing the number of photons that can be trapped. As a result, the detectivity in the multichannel PMT 49 can be improved.

The objective lens 41 may be configured by combining a plurality of lenses different in shape and characteristics. For example, in the case that the objective lens 41 is configured by ten lenses of eight groups, the objective lens 41 preferably has an overall length of 30 mm or less, an operating distance of 0.5 mm or more, and a telecentric characteristic (inclination angle of rays of emergent light from the lens with respect to its optical axis) of 1° or less. Further, the objective lens 41 preferably has an average transmittance of 90% or more to the light having a wavelength range of at least 500 to 800 nm, a wavefront aberration of 60 mλrms or less and a curvature of field of 1 μm or less in the field having a diameter of 150 μm.

As in the telecentric condenser lens 48 mentioned above, each lens constituting the objective lens 41 may be provided by a lens formed of a glass material having a large refractive index and a large Abbe number. In this case, a degradation in aberration can be suppressed and the transmittance can be greatly improved. Further, an AR coating of multiple layers may be formed on the surface of each lens constituting the objective lens 41. In this case, the reflectance of each lens to the light having a wavelength range of 500 to 800 nm can be reduced to thereby improve the detection efficiency.

Operation of the Optical Measuring Device 1

There will now be described the operation of the optical measuring device 1, i.e., a method of optically measuring a sample such as cells or microbeads by using the optical measuring device 1. The sample to be measured by the optical measuring device 1 may be modified by one or more fluorochromes.

In the optical measuring device 1 according to this embodiment, a sample is allowed to flow in the channel formed in the channel chip 2, and the laser light 5 emitted from the laser light source 31 in the light applying section 3 is condensed by the objective lens 36 and applied to the sample. The fluorescence 6 generated from the sample is trapped by the objective lens 41 in the fluorescence detecting section 4. Further, any disturbance components other than the fluorescence 6 generated from the sample are removed by the band-cut filter 42 and the pinhole 44. Thereafter, the fluorescence 6 is separated according to wavelengths by the transmission grating 47, and the separated light beams having different wavelengths are condensed through the telecentric condenser lens 48 to the respective detection channels of the multichannel PMT 49.

In the optical measuring device 1 according to an embodiment, the light beams separated by the transmission grating 47 are condensed through the telecentric condenser lens 48 to the respective detection channels of the multichannel PMT 49. Accordingly, the detection efficiency can be improved with a small space for installation and a small number of parts. Thus, although the multichannel PMT 49 is used as a detector, the fluorescence 6 generated from the sample can be detected with high sensitivity and the device can be made compact as a whole.

Further, the transmittance of the telecentric condenser lens 48 to the light having a wavelength range of at least 500 to 800 nm is set to 90% or more, thereby improving the detectivity. In addition, the objective lens 41 for trapping the fluorescence 6 generated from the sample has a wide field and a high numerical aperture, thereby further improving the detectivity.

The optical measuring device 1 according to this embodiment may be used as a flow cytometry device, beads assay device, etc.

General Configuration of the Optical Measuring Device

Figure 5:
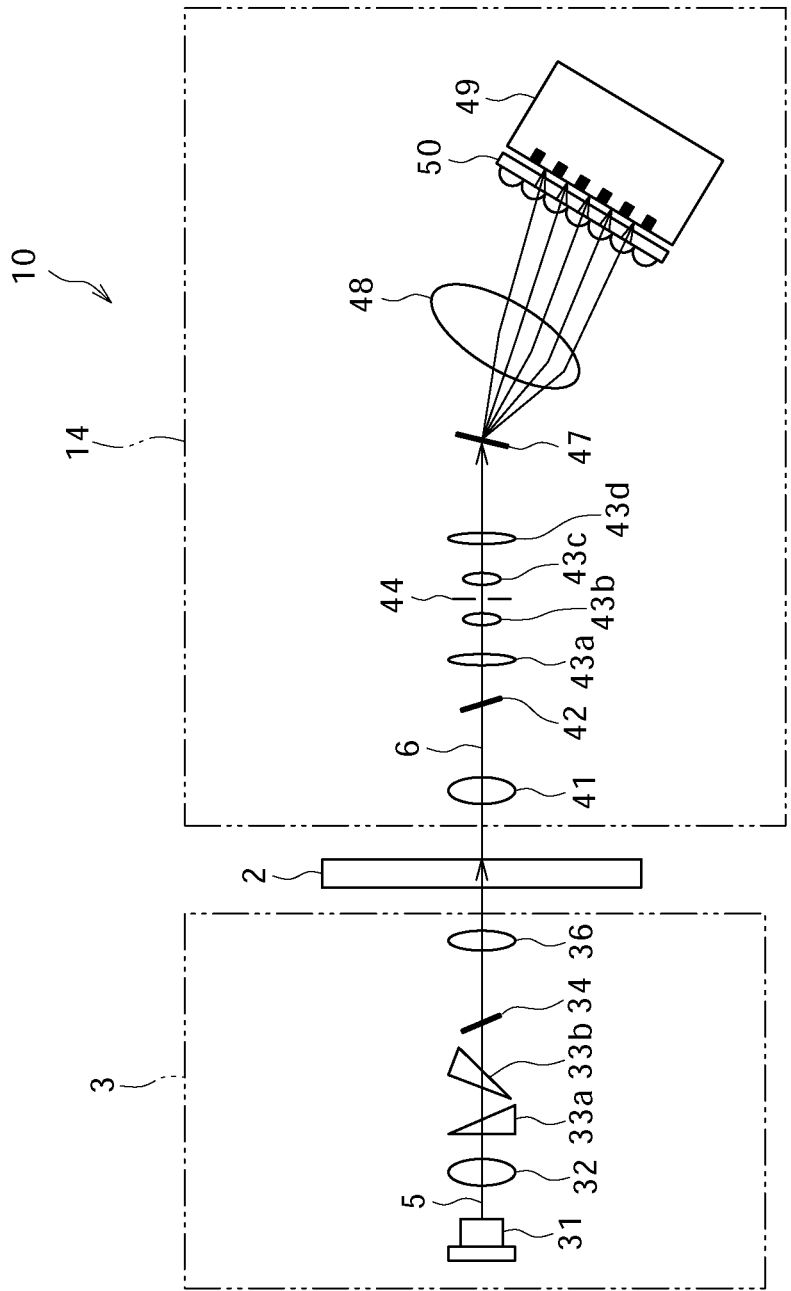
FIG. 5 is a schematic diagram showing the configuration of an optical measuring device according to a second embodiment.

An optical measuring device according to a second embodiment will now be described. FIG. 5 is a schematic diagram showing the configuration of an optical measuring device 10 according to the second embodiment. In FIG. 5, the same parts as those of the optical measuring device 1 according to the first embodiment shown in FIG. 1 are denoted by the same reference symbols and the detailed description thereof will be omitted herein. As shown in FIG. 5, the optical measuring device 10 according to the second embodiment is similar to the optical measuring device 1 according to the first embodiment except that a microlens array 50 is provided in a fluorescence detecting section 14.

Configuration of the Fluorescence Detecting Section 14

The fluorescence detecting section 14 in the optical measuring device 10 according to this embodiment includes the microlens array 50 located between a telecentric condenser lens 48 and a multichannel PMT 49. In the optical measuring device 10, the light beams emerging from the telecentric condenser lens 48 are condensed through the microlens array 50 to the respective detection channels of the multichannel PMT 49.

Microlens Array 50

Figure 6:
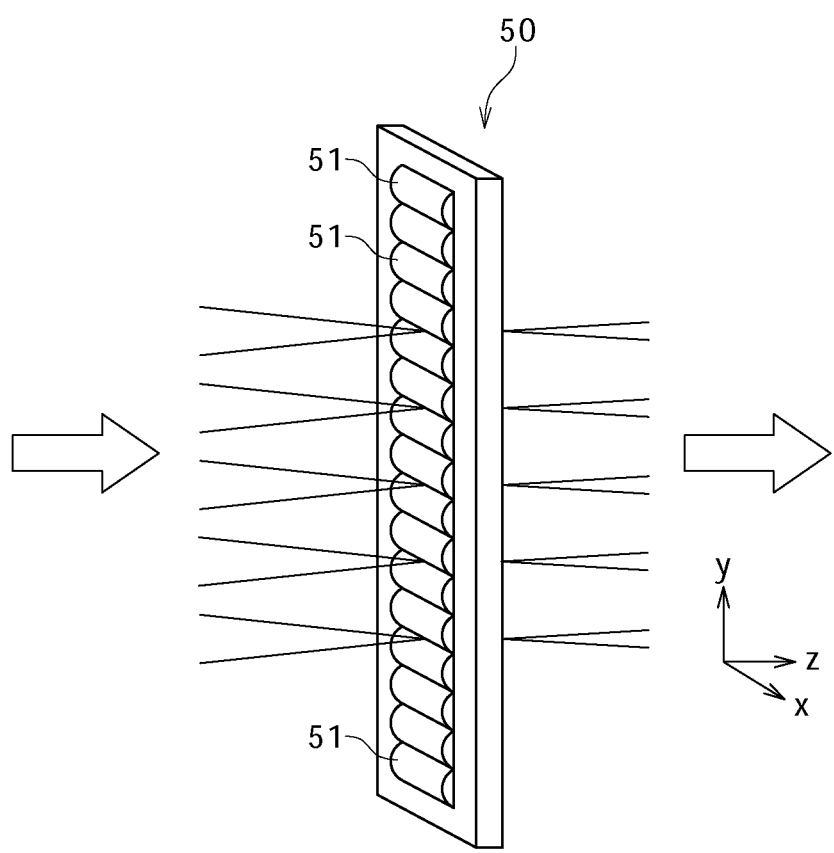
FIG. 6 is a perspective view schematically showing the condition that light beams are incident on a microlens array used in the optical measuring device shown in FIG. 5.

FIG. 6 is a perspective view schematically showing the condition that the light beams are incident on the microlens array 50. As shown in FIG. 6, the microlens array 50 provided in the fluorescence detecting section 14 may be configured by a plurality of cylindrical lenses 51 arranged so that the axes thereof extending in the X direction as viewed in FIG. 6 are parallel to each other. The number of the cylindrical lenses 51 corresponds to the number of the detection channels of the multichannel PMT 49. Further, the direction of arrangement of the cylindrical lenses 51 constituting the microlens array 50 (the Y direction as viewed in FIG. 6) coincides with the direction of arrangement of the detection channels of the multichannel PMT 49.

In the case that the multichannel PMT 49 has 32 slit-shaped detection channels each having a size of 0.7 mm×2.5 mm and that these detection channels are arranged in a line with a pitch of 1 mm, mere projection of image forming light to the multichannel PMT 49 results in that the image forming light cannot be detected over the opening rate (70%) of the detection channels (detection windows). To cope with this problem, in the case that the microlens array 50 having 34 cylindrical lenses 51 each having a width of 1 mm is located just before the 32 detection channels of the multichannel PMT 49, the light beams that should be blocked can be refracted to enter the detection channels.

As a result, the detection efficiency of the multichannel PMT 49 can be improved. The reason for arrangement of the 34 cylindrical lenses 51 for the 32 detection channels is to suppress the influence of possible distortion in shape of the outermost two lenses in the case that the microlens array 50 is formed by injection molding of resin.

As mentioned above, a dead zone is present between any adjacent ones of the detection channels of the multichannel PMT 49. In the optical measuring device 10 according to this embodiment, the microlens array 50 is located just before the detecting surface of the multichannel PMT 49 as shown in FIG. 6. With this arrangement, all of the light beams from the telecentric condenser lens 48 can be guided to the respective detection channels of the multichannel PMT 49 as avoiding the dead zones. Accordingly, the fluorescence 6 generated from the sample can be detected efficiently. In the case that the focal points of the telecentric condenser lens 48 are positioned at the joints of the cylindrical lenses 51 of the microlens array 50, crosstalk between any adjacent ones of the detection channels of the multichannel PMT 49 can be minimized.

Operation of the Optical Measuring Device 10

There will now be described the operation of the optical measuring device 10, i.e., a method of optically measuring a sample such as cells or microbeads by using the optical measuring device 10. In the optical measuring device 10, a sample is allowed to flow in the channel formed in the channel chip 2, and the laser light 5 emitted from the laser light source 31 in the light applying section 3 is condensed by the objective lens 36 and applied to the sample.

The fluorescence 6 generated from the sample is trapped by the objective lens 41 in the fluorescence detecting section 14. Further, any disturbance components other than the fluorescence 6 generated from the sample are removed by the band-cut filter 42 and the pinhole 44. Thereafter, the fluorescence 6 is separated according to wavelengths by the transmission grating 47, and the separated light beams having different wavelengths are condensed through the telecentric condenser lens 48 to the microlens array 50.

Figure 7A:
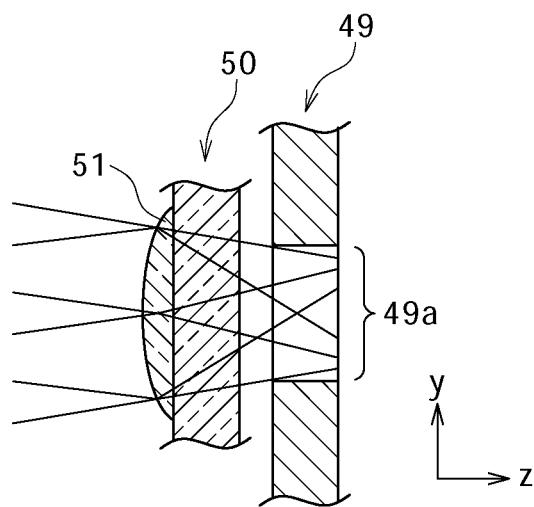
FIG. 7A is an enlarged sectional view schematically showing a change in optical path of the light beams incident on the microlens array shown in FIG. 5 as taken in the direction of the axis of each cylindrical lens constituting the microlens array.
Figure 7B:
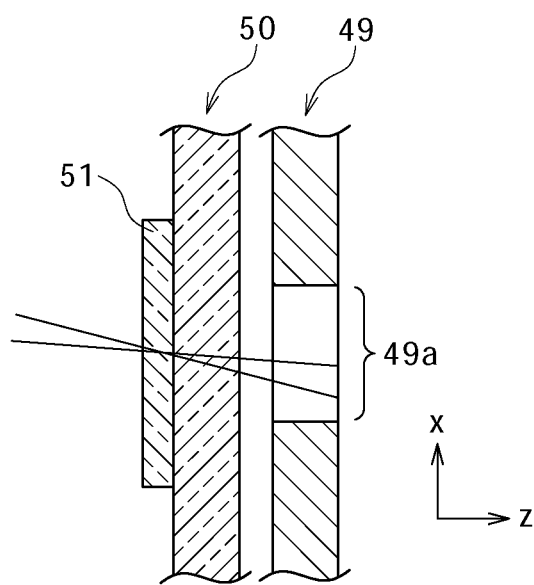
FIG. 7B is a view as taken in the direction of arrangement of the cylindrical lenses.

FIGS. 7A and 7B are enlarged sectional views schematically showing a change in optical path of the light beams incident on the microlens array 50. FIG. 7A is a view taken in the direction of the axis of each cylindrical lens 51 (i.e., in the X direction as viewed in FIG. 6), and FIG. 7B is a view taken in the direction of arrangement of the cylindrical lenses 51 (i.e., in the Y direction as viewed in FIG. 6). As shown in FIGS. 7A and 7B, the light beams incident on the microlens array 50 are condensed to the detection channels 49a of the multichannel PMT 49 by the cylindrical lenses 51. Thus, by locating the microlens array 50 just before the detecting surface of the multichannel PMT 49, the light beams separated according to wavelengths can be guided to the detection channels of the multichannel PMT 49 as avoiding the dead zones.

In the optical measuring device 10 according to this embodiment, the microlens array 50 is provided between the telecentric condenser lens 48 and the multichannel PMT 49. With this arrangement, the efficiency of incidence of light to each detection channel can be improved. As a result, the detectivity in the multichannel PMT 49 can be further improved.

The other configuration and effect in the optical measuring device 10 are similar to those in the first embodiment.

General Configuration of the Optical Measuring Device

Figure 8:
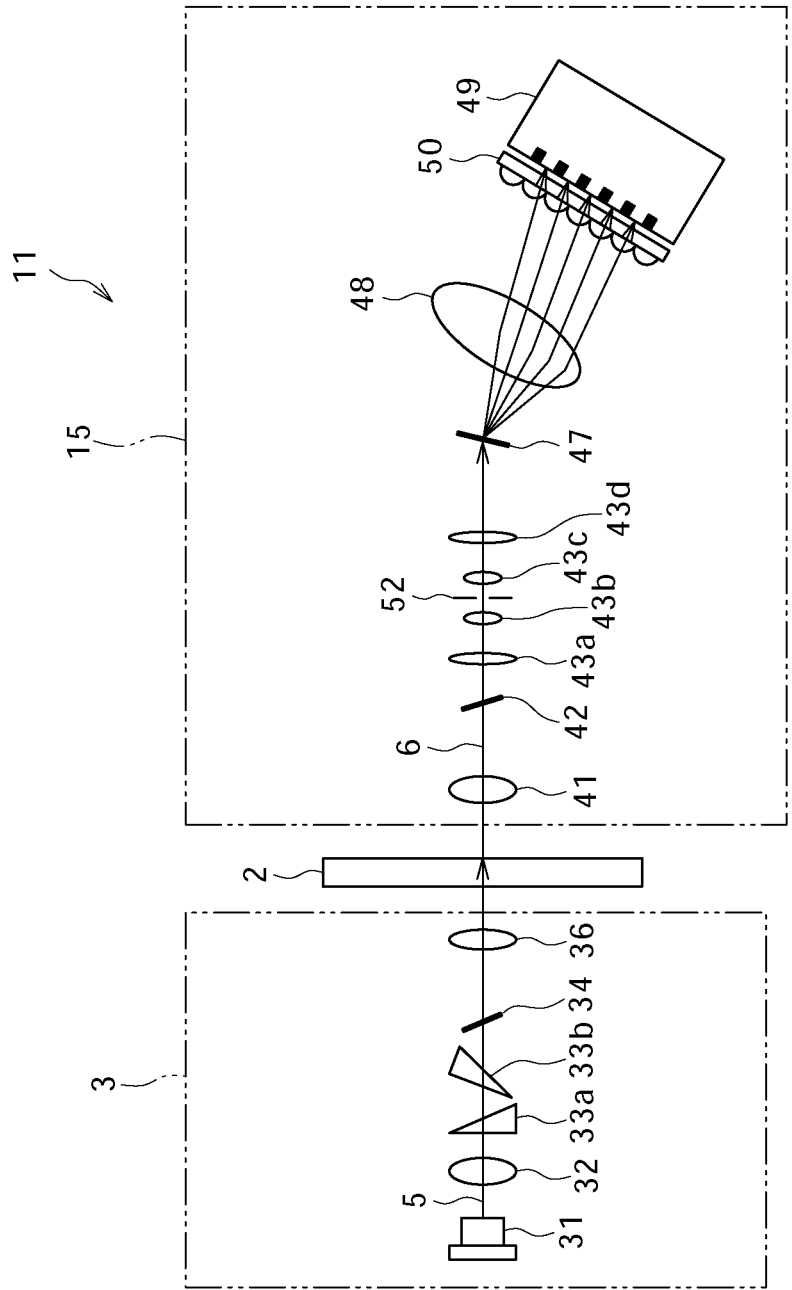
FIG. 8 is a schematic diagram showing the configuration of an optical measuring device according to a third embodiment.

An optical measuring device according to a third embodiment will now be described. FIG. 8 is a schematic diagram showing the configuration of an optical measuring device 11 according to the third embodiment. In FIG. 8, the same parts as those of the optical measuring device 10 according to the second embodiment shown in FIG. 5 are denoted by the same reference symbols and the detailed description thereof will be omitted herein. As shown in FIG. 8, the optical measuring device 11 according to the third embodiment is similar to the optical measuring device 10 according to the second embodiment except that a slit 52 is provided in place of the pinhole 44 in a fluorescence detecting section 15.

Configuration of the Fluorescence Detecting Section 15

The fluorescence detecting section 15 in the optical measuring device 11 according to this embodiment includes the rectangular slit 52 located between an objective lens 41 and a transmission grating 47 in such a manner that the longitudinal direction of the rectangular slit 52 is parallel to the flowing direction of the sample. As mentioned above, when a pinhole is used to remove a disturbance component generated from any matter other than the sample, it is difficult to reduce a noise component and simultaneously to improve the detectivity. To the contrary, when the rectangular slit 52 is used in place of such a pinhole, the opening size of the rectangular slit 52 can be increased in only the flowing direction of the sample. Accordingly, unwanted light can be cut off and the fluorescence 6 from the sample can be trapped at the maximum.

Slit 52

FIG. 9 is a plan view schematically showing the configuration of the slit 52. As shown in FIG. 9, the slit 52 provided in the optical measuring device 11 according to this embodiment has a rectangular opening extending in the flowing direction of the sample. For example, the length l of this rectangular opening is 0.2 to 1.5 mm and the width w of this opening is 0.4 mm or less. If the opening length l is less than 0.2 mm, the light quantity is reduced to cause a reduction in detectivity. If the opening length l is greater than 1.5 mm or the opening width w is greater than 0.4 mm, a noise component is increased to cause a reduction in detectivity.

Operation of the Optical Measuring Device 11

There will now be described the operation of the optical measuring device 11, i.e., a method of optically measuring a sample such as cells or microbeads by using the optical measuring device 11. In the optical measuring device 11, a sample is allowed to flow in the channel formed in the channel chip 2, and the laser light 5 emitted from the laser light source 31 in the light applying section 3 is condensed by the objective lens 36 and applied to the sample.

The fluorescence 6 generated from the sample is trapped by the objective lens 41 in the fluorescence detecting section 15. Further, any disturbance components other than the fluorescence 6 generated from the sample are removed by the band-cut filter 42 and the slit 52. Thereafter, the fluorescence 6 is separated according to wavelengths by the transmission grating 47, and the separated light beams having different wavelengths are condensed through the telecentric condenser lens 48 and the microlens array 50 to the detection channels of the multichannel PMT 49.

In the optical measuring device 11 according to this embodiment, the rectangular slit 52 is arranged in such a manner that the longitudinal direction of the rectangular slit 52 is parallel to the flowing direction of the sample. Accordingly, unwanted light can be cut off and the fluorescence 6 from the sample can be trapped at the maximum. As a result, the efficiency of incidence of light to each detection channel of the multichannel PMT 49 can be improved to thereby improve the detectivity.

The other configuration and effect in the optical measuring device 11 are similar to those in the first and second embodiments.

General Configuration of the Optical Measuring Device

Figure 10:
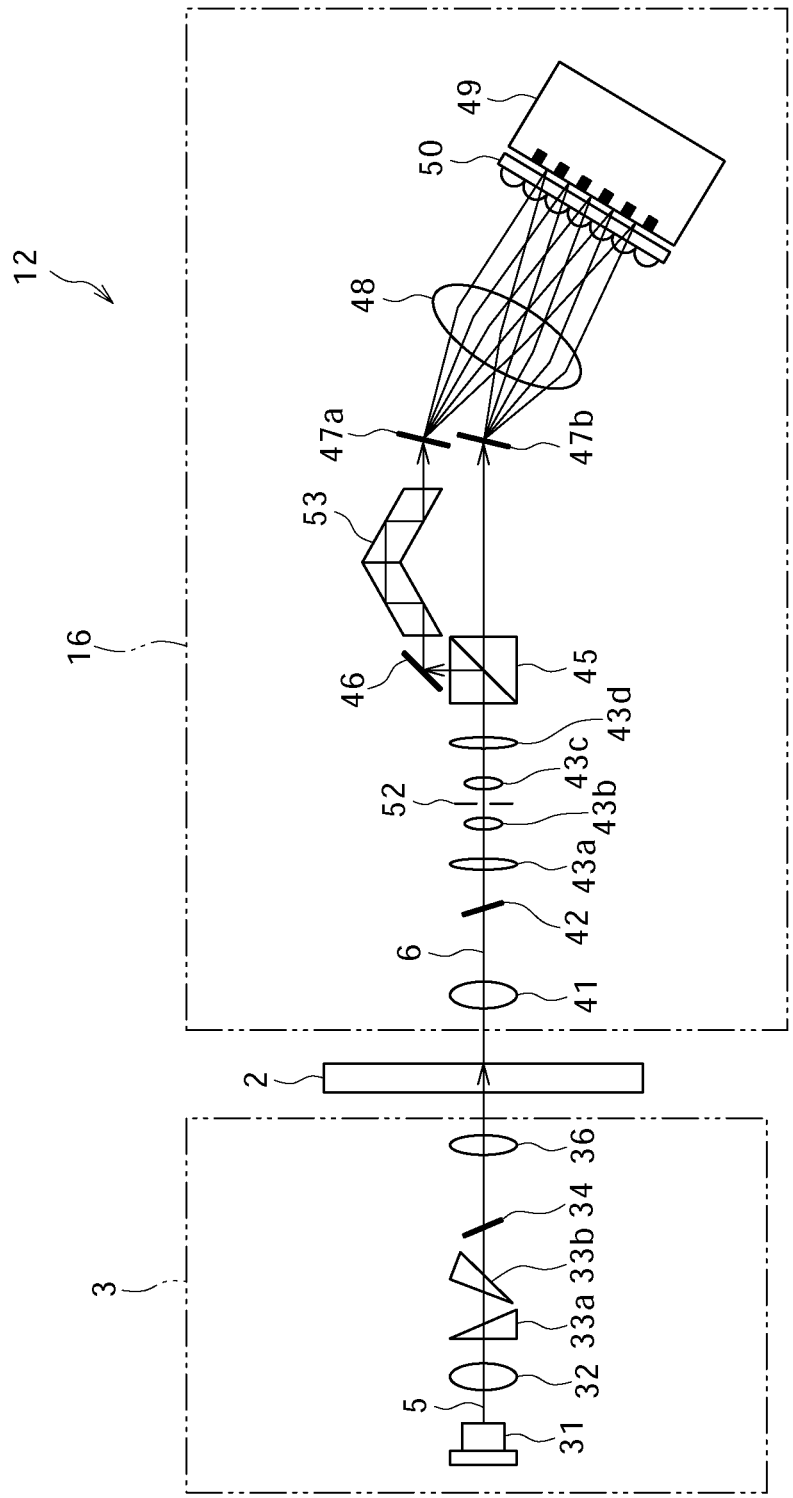
FIG. 10 is a schematic diagram showing the configuration of an optical measuring device according to a fourth embodiment.

An optical measuring device according to a fourth embodiment will now be described. FIG. 10 is a schematic diagram showing the configuration of an optical measuring device 12 according to the fourth embodiment. In FIG. 10, the same parts as those of the optical measuring device 11 according to the third embodiment shown in FIG. 8 are denoted by the same reference symbols and the detailed description thereof will be omitted herein. As shown in FIG. 10, the optical measuring device 12 is configured so that the fluorescence 6 is separated into a parallel polarized light component and an orthogonal polarized light component in a fluorescence detecting section 16, and that one of these polarized light components is rotated to make the polarization direction of this polarized light component coincide with the polarization direction of the other. Thereafter, these two light beams having the same polarization direction are imaged by a telecentric condenser lens 48.

Configuration of the Fluorescence Detecting Section 16

The fluorescence detecting section 16 in the optical measuring device 12 according to this embodiment includes a polarization beam splitter 45 and a Fresnel rhomb 53 in addition to the components of the fluorescence detecting section 15 of the optical measuring device 11 according to the third embodiment. Further, the fluorescence detecting section 16 includes two transmission gratings 47a and 47b in place of the transmission grating 47 in the fluorescence detecting section 16 shown in FIG. 8. One of the two polarized light components from the polarization beam splitter 45 is directly incident on the transmission grating 47b, and the other polarized light component is rotated in polarization direction by the Fresnel rhomb 53 to enter the transmission grating 47a.

Further, the fluorescence detecting section 16 may further include a mirror 46 interposed between the polarization beam splitter 45 and the Fresnel rhomb 53 for introducing one of the two polarized light components emerged from the polarization beam splitter 45 into the Fresnel rhomb 53. The other configuration in the fluorescence detecting section 16 is similar to that in the fluorescence detecting section 15 shown in FIG. 8. (Polarization beam splitter 45)

Figure 11:
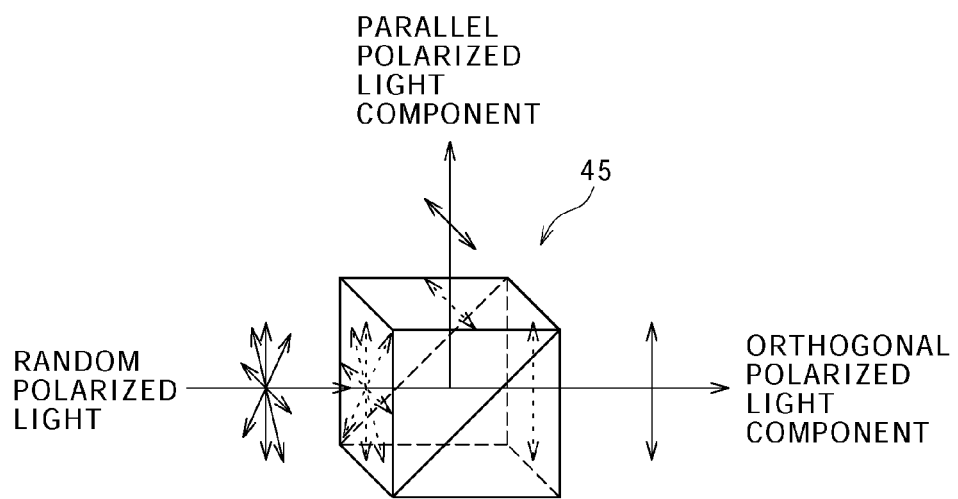
FIG. 11 is a schematic diagram showing the operation of a polarization beam splitter used in the optical measuring device shown in FIG. 10.

FIG. 11 is a schematic diagram showing the operation of the polarization beam splitter 45. As shown in FIG. 11, the polarization beam splitter 45 functions to separate incident light into a parallel polarized light component and an orthogonal polarized light component. The polarization beam splitter 45 used in the optical measuring device 12 is essentially capable of separating the light having a wavelength range of 450 to 800 nm, so that the loss due to light separation can be suppressed. Further, the polarization beam splitter 45 is preferably capable of separating the light having a wavelength range of 400 to 800 nm by improving the wavelength band characteristic of a reflecting surface. (Fresnel rhomb 53)

Figure 12:
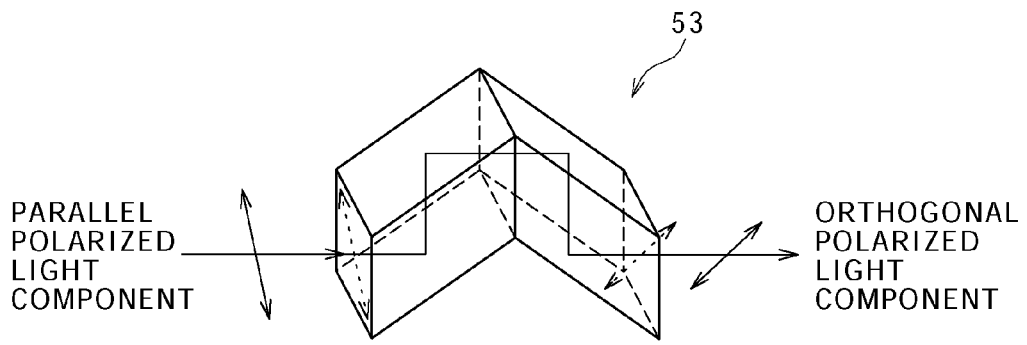
FIG. 12 is a schematic diagram showing the operation of a Fresnel rhomb shown in FIG. 10.

FIG. 12 is a schematic diagram showing the operation of the Fresnel rhomb 53. The Fresnel rhomb 53 functions to convert linearly polarized light into circularly polarized light. As shown in FIG. 12, the polarization direction of the parallel polarized light component can be rotated 90° by twice passing this polarized light component through the Fresnel rhomb 53. In other words, the parallel polarized light component reflected by the polarization beam splitter 45 can be converted into an orthogonal polarized light component by the Fresnel rhomb 53.

Operation of the Optical Measuring Device 12

There will now be described the operation of the optical measuring device 12, i.e., a method of optically measuring a sample such as cells or microbeads by using the optical measuring device 12. In the optical measuring device 12, a sample is allowed to flow in the channel formed in the channel chip 2, and the laser light 5 emitted from the laser light source 31 in the light applying section 3 is condensed by the objective lens 36 and applied to the sample.

The fluorescence 6 generated from the sample is trapped by the objective lens 41 in the fluorescence detecting section 16. Further, any disturbance components other than the fluorescence 6 generated from the sample are removed by the band-cut filter 42 and the slit 52. Thereafter, the fluorescence 6 is separated into a parallel polarized light component and an orthogonal polarized light component by the polarization beam splitter 45. The orthogonal polarized light component is directly emerged toward the transmission grating 47b. On the other hand, the parallel polarized light component is reflected on the mirror 46 to enter the Fresnel rhomb 53, and is rotated 90° in polarization direction in the Fresnel rhomb 53, so that the polarization direction of this linearly polarized light coincides with the polarization direction of the orthogonal polarized light component. This parallel polarized light component rotated in the Fresnel rhomb 53 is emerged toward the transmission grating 47a.

Thereafter, the two light beams having the polarization direction of the orthogonal polarized light component are respectively separated by the transmission gratings 47a and 47b to obtain two layers of sectorially diverging spectral light. These two layers of spectral light are imaged by the telecentric condenser lens 48 and next condensed through the microlens array 50 to the detection channels of the multichannel PMT 49.

While the parallel polarized light component of the fluorescence 6 is converted into an orthogonal polarized light component in this embodiment, the orthogonal polarized light component of the fluorescence 6 may be converted into a parallel polarized light component by suitably changing the locations of the polarization beam splitter 45 and the Fresnel rhomb 53.

The diffraction efficiency of the diffraction grating (the transmission gratings 47a and 47b) for separating the fluorescence 6 according to specific wavelengths changes according to the polarization of incident light, so that it is difficult to obtain high diffraction efficiency for both P-polarized light and S-polarized light at a time. For example, it is possible to relatively easily increase the diffraction efficiency of a polarized light component in one direction, particularly an S-polarized light component of the light incident on the diffraction grating. In this case, however, the loss of the other polarized light component is increased. To cope with this problem, the polarized light component whose loss becomes large may be rotated 90° in polarization direction to make the polarization direction coincide with that of the polarized light component which is higher in diffraction efficiency, thereby utilizing the diffraction efficiency at the maximum. However, it is difficult to rotate the fluorescence having a wide wavelength band at the same rotational angle by using a normal wave plate.

To the contrary, the optical measuring device 12 according to this embodiment uses the polarization beam splitter 45 capable of separating the light having a wide wavelength band corresponding to the wavelength band for use in spectral detection. Accordingly, the separation of polarized light components can be attained in the condition where the loss of the fluorescence 6 at any wavelength can be suppressed at the maximum. Further, since the Fresnel rhomb 53 is used, the polarization direction of the incident polarized light component can be rotated 90° with little influence of wavelength change to thereby make the polarization direction coincide with that of S-polarized light or P-polarized light. Accordingly, the polarization direction of the P-polarized light component or the S-polarized light component of the fluorescence 6 can be converted to the polarization direction of the polarized light component which is higher in diffraction efficiency. As a result, the efficiency of incidence on each detection channel can be improved to thereby improve the detectivity in the multichannel PMT 49.

The other configuration and effect in the optical measuring device 12 are similar to those in the first to third embodiments.

General Configuration of the Optical Measuring Device

Figure 13:
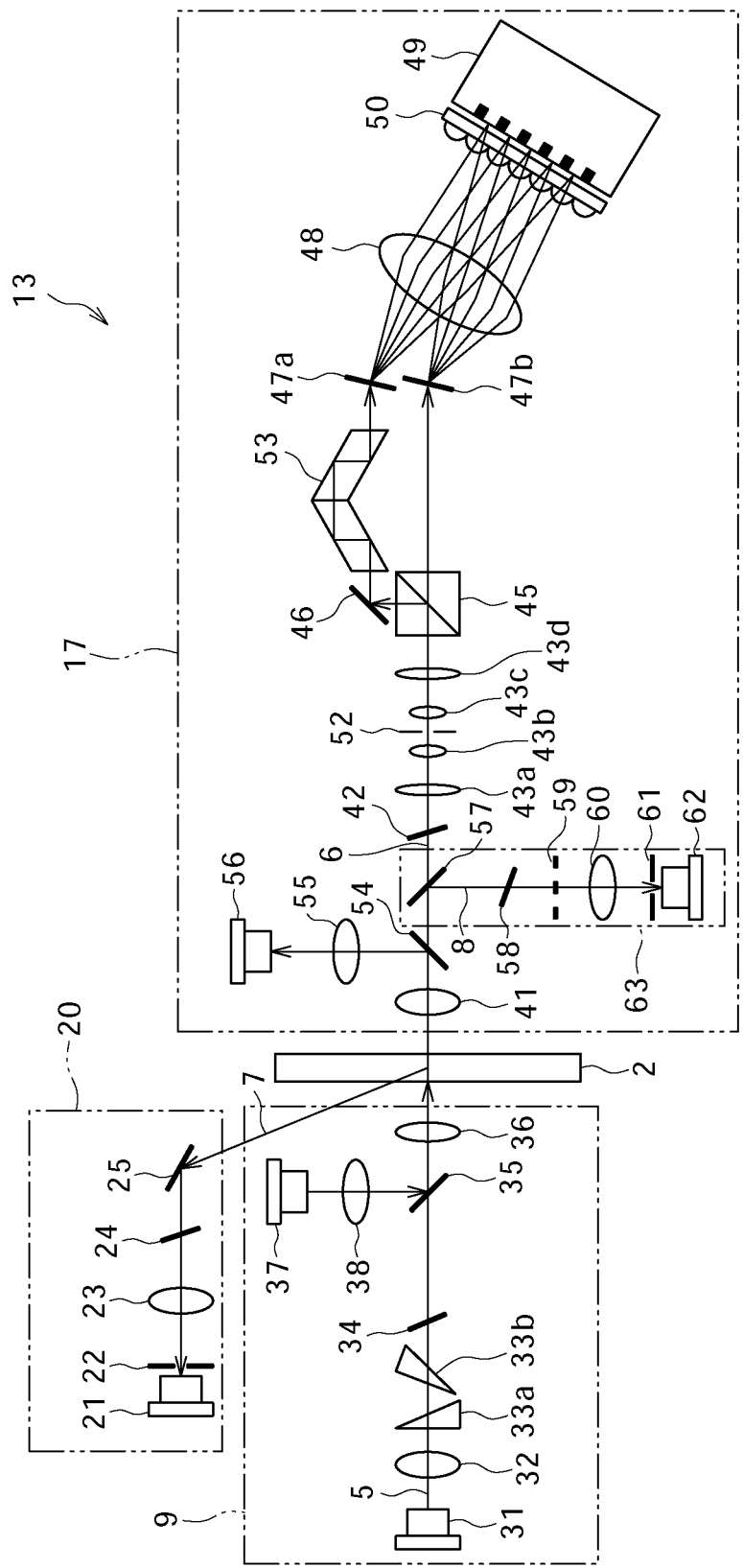
FIG. 13 is a schematic diagram showing the configuration of an optical measuring device according to a fifth embodiment.

An optical measuring device according to a fifth embodiment will now be described. FIG. 13 is a schematic diagram showing the configuration of an optical measuring device 13 according to the fifth embodiment. In FIG. 13, the same parts as those of the optical measuring device 12 according to the fourth embodiment shown in FIG. 10 are denoted by the same reference symbols and the detailed description thereof will be omitted herein. As shown in FIG. 13, the optical measuring device 13 includes two scattered light detecting sections 20 and 63 for detecting scattered lights 7 and 8 generated from a sample flowing in a channel in addition to a light applying section 9 for applying laser light 5 to the sample and a fluorescence detecting section 17 for detecting fluorescence 6 generated from the sample. As in the optical measuring device according to each embodiment mentioned above, the optical measuring device 13 uses a channel chip 2 having an internal minute channel to measure the sample flowing in this channel.

Configuration of the Light Applying Section 9

The light applying section 9 in the optical measuring device 13 according to this embodiment includes an auxiliary light source 37 for emitting light (illuminating light) for monitoring a portion irradiated with exciting light (laser light 5) by using a CCD (Charge Coupled Device) 56. For example, in the case that a laser diode is used for the laser light source 31, an LED or a halogen lamp may be used for the auxiliary light source 37. Further, the light applying section 9 may further include a condenser lens 38 and a short-pass filter 35 in association with the auxiliary light source 37. The short-pass filter 35 is an optical filter having such characteristics that it passes light having short wavelengths, such as the laser light 5 and reflects light having long wavelengths. For example, the short-pass filter 35 is located between the bandpass filter 34 and the objective lens 36. In this case, the light emitted from the auxiliary light source 37 is condensed by the condenser lens 38 and next reflected by the short-pass filter 35 to enter the objective lens 36. The other configuration in the light applying section 9 is similar to that in the light applying section 3 of the optical measuring device 1 according to the first embodiment.

Configuration of the Scattered Light Detecting Sections 20 and 63

The scattered light detecting section 20 functions to detect the side scattered light 7 generated from the sample. For example, the scattered light detecting section 20 may be composed of a mirror 25, bandpass filter 24, lens 23, pinhole 22, and PMT 21 arranged in this order in the traveling direction of the scattered light 7. The PMT 21 is a detector for detecting the scattered light 7, and has one or more detection channels. The bandpass filter 24 and the pinhole 22 function to remove any disturbance components other than the scattered light 7, thereby improving the detectivity. Further, the mirror 25 and the lens 23 function to introduce the scattered light 7 into the PMT 21.

On the other hand, the scattered light detecting section 63 functions to detect the forward scattered light 8 generated from the sample, and has an optical path partially common to the optical path in the fluorescence detecting section 17. More specifically, a long-pass filter 57 for separating the fluorescence 6 and the forward scattered light 8 is provided between the objective lens 41 and the band-cut filter 42 of the fluorescence detecting section 17. The forward scattered light 8 separated by the long-pass filter 57 is passed through a bandpass filter 58, a mask 59, a lens 60, and a pinhole 61 in this order to enter a photodiode 62 as a detector.

Configuration of the Fluorescence Detecting Section 17

The fluorescence detecting section 17 of the optical measuring device 13 includes a beam splitter 54 for separating the light emitted from the auxiliary light source 37 from the fluorescence 6. The beam splitter 54 is located between the objective lens 41 and the band-cut filter 42. The light emitted from the auxiliary light source 37 and separated from the fluorescence 6 by the beam splitter 54 is passed through a lens 55 to enter the CCD 56 for monitoring the portion irradiated with the exciting light. The other configuration in the fluorescence detecting section 17 is similar to that in the fluorescence detecting section 16 of the optical measuring device 12 according to the fourth embodiment.

Operation of the Optical Measuring Device 13

There will now be described the operation of the optical measuring device 13, i.e., a method of optically measuring a sample such as cells or microbeams by using the optical measuring device 13. In the optical measuring device 13, the laser light 5 emitted from the laser light source 31 in the light applying section 9 is passed through the condenser lens 32 and the anamorphic lenses 33a and 33b, and unwanted light components are removed by the bandpass filter 34. Thereafter, the laser light 5 is passed through the short-pass filter 35 to enter the objective lens 36. The laser light 5 is condensed by the objective lens 36 and applied to the sample flowing in the channel formed in the channel chip 2.

In addition to the laser light 5, the light for illuminating the portion irradiated with the laser light 5 is also applied to the sample. More specifically, the light emitted from the auxiliary light source 37 is condensed by the condenser lens 38 and reflected by the short-pass filter 35 to enter the objective lens 36. As similar to the laser light 5, the light reflected by the short-pass filter 35 is condensed by the objective lens 36 and applied to the portion irradiated with the exciting light (laser light 5).

The fluorescence 6 and the scattered lights 7 and 8 generated from the sample irradiated with the laser light 5 are detected in the fluorescence detecting section 17 and the scattered light detecting sections 20 and 63, respectively. More specifically, the light generated from the sample is trapped by the objective lens 41 in the fluorescence detecting section 17, and the light emitted from the auxiliary light source 37 is separated from the above light including the fluorescence 6 by the beam splitter 54. Thereafter, the light reflected by the beam splitter 54 (the light emitted from the auxiliary light source 37) is condensed by the condenser lens 55 and monitored by the CCD 56. On the other hand, the light transmitted through the beam splitter 54 is further separated into the light having longer wavelengths (the fluorescence 6) and the light having shorter wavelengths (the forward scattered light 8) by the long-pass filter 57. The forward scattered light 8 reflected by the long-pass filter 57 is passed through the bandpass filter 58, the mask 59, the lens 60, and the pinhole 61 and detected by the photodiode 62.

The light transmitted through the long-pass filter 57 is passed through the band-cut filter 42 and the slit 52 to remove any disturbance components other than the fluorescence 6 generated from the sample. Thereafter, the fluorescence 6 is separated into a parallel polarized light component and an orthogonal polarized light component by the polarization beam splitter 45. The orthogonal polarized light component transmitted through the polarization beam splitter 45 is directly incident on the transmission grating 47b, whereas the parallel polarized light component reflected by the polarization beam splitter 45 is reflected on the mirror 46 to enter the Fresnel rhomb 53. The parallel polarized light component is rotated 90° as linearly polarized light in the Fresnel rhomb 53, so that the polarization direction of the parallel polarized light component thus rotated coincides with the polarization direction of the orthogonal polarized light component and enters the transmission grating 47a.

Thereafter, the two light beams having the polarization direction of the orthogonal polarized light component are respectively separated by the transmission gratings 47a and 47b to obtain two layers of sectorially diverging spectral light. These two layers of spectral light are imaged by the telecentric condenser lens 48 and next condensed through the microlens array 50 to the detection channels of the multichannel PMT 49.

The optical measuring device 13 according to this embodiment includes the scattered light detecting sections 20 and 63 in addition to the fluorescence detecting section 17. Accordingly, more information on the sample can be obtained. The other configuration and effect in the optical measuring device 13 are similar to those in the first to fourth embodiments.

General Configuration of the Optical Measuring Device

Figure 14:
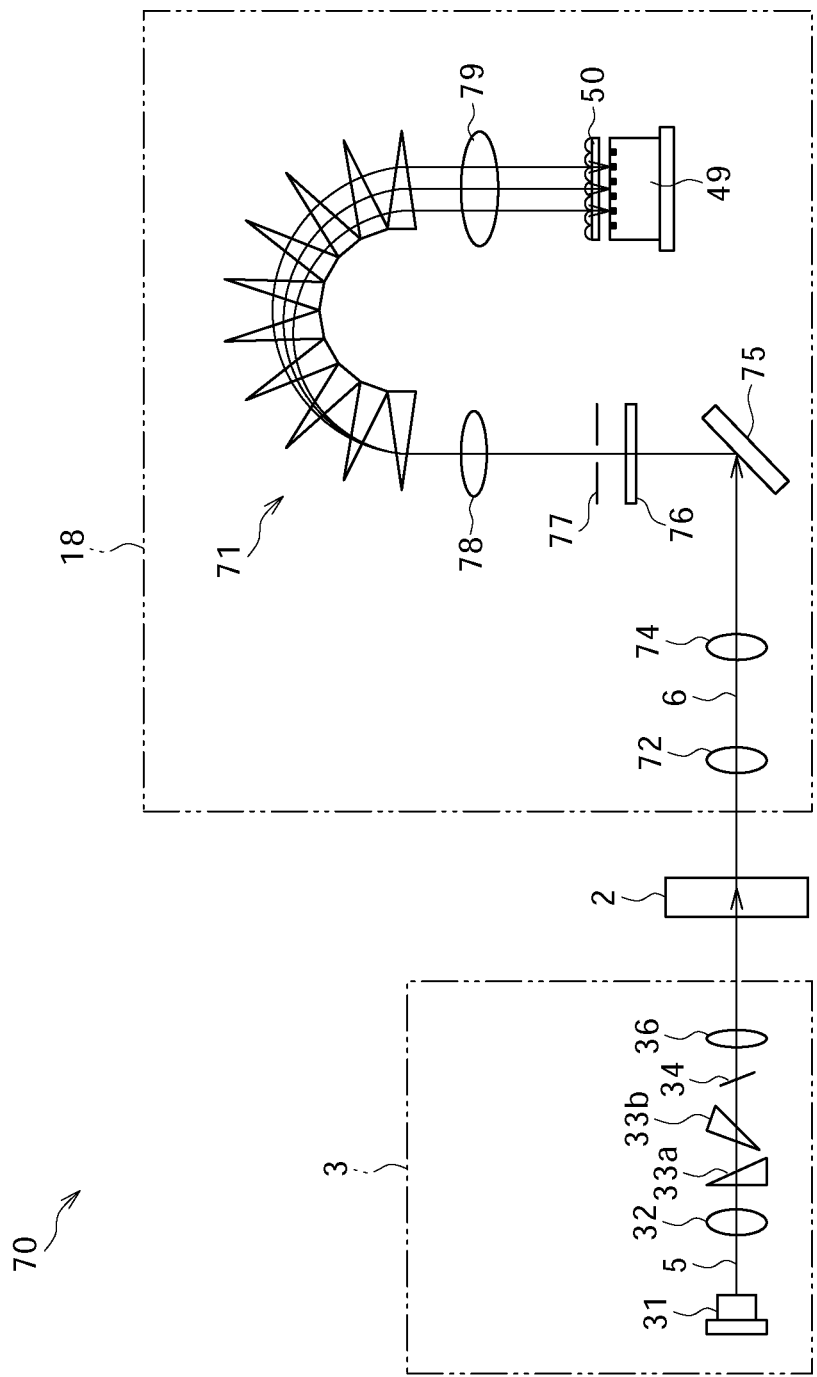
FIG. 14 is a schematic diagram showing the configuration of an optical measuring device according to a sixth embodiment.

An optical measuring device according to a sixth embodiment will now be described. FIG. 14 is a schematic diagram showing the configuration of an optical measuring device 70 according to the sixth embodiment. In FIG. 14, the same parts as those of the optical measuring device according to any one of the first to fifth embodiments mentioned above are denoted by the same reference symbols and the detailed description thereof will be omitted herein. As shown in FIG. 14, the optical measuring device 70 includes a light applying section 3 for applying laser light 5 to a sample flowing in a channel provided in a channel chip 2 and a fluorescence detecting section 18 for detecting fluorescence 6 generated from the sample irradiated with the laser light 5.

Configuration of the Fluorescence Detecting Section 18

The fluorescence detecting section 18 in the optical measuring device 70 essentially includes a light separator 71 for separating the fluorescence 6 generated from the sample according to wavelengths, a multichannel PMT 49 as a detector, and a telecentric condenser lens 79 interposed between the light separator 71 and the multichannel PMT 49. Preferably, the fluorescence detecting section 18 further includes an objective lens 72 for condensing the fluorescence 6 generated from the sample and a pinhole 77 for removing a disturbance component generated from any matter other than the sample. Further, as demanded, the fluorescence detecting section 18 may further include a condenser lens 74, a mirror 75, and a filter 76 provided between the objective lens 72 and the pinhole 77 and also include a collimator lens 78 provided between the pinhole 77 and the light separator 71. The collimator lens 78 functions to convert divergent rays of light emerging from the pinhole 77 into parallel rays of light.

Light Separator 71

Figure 15:
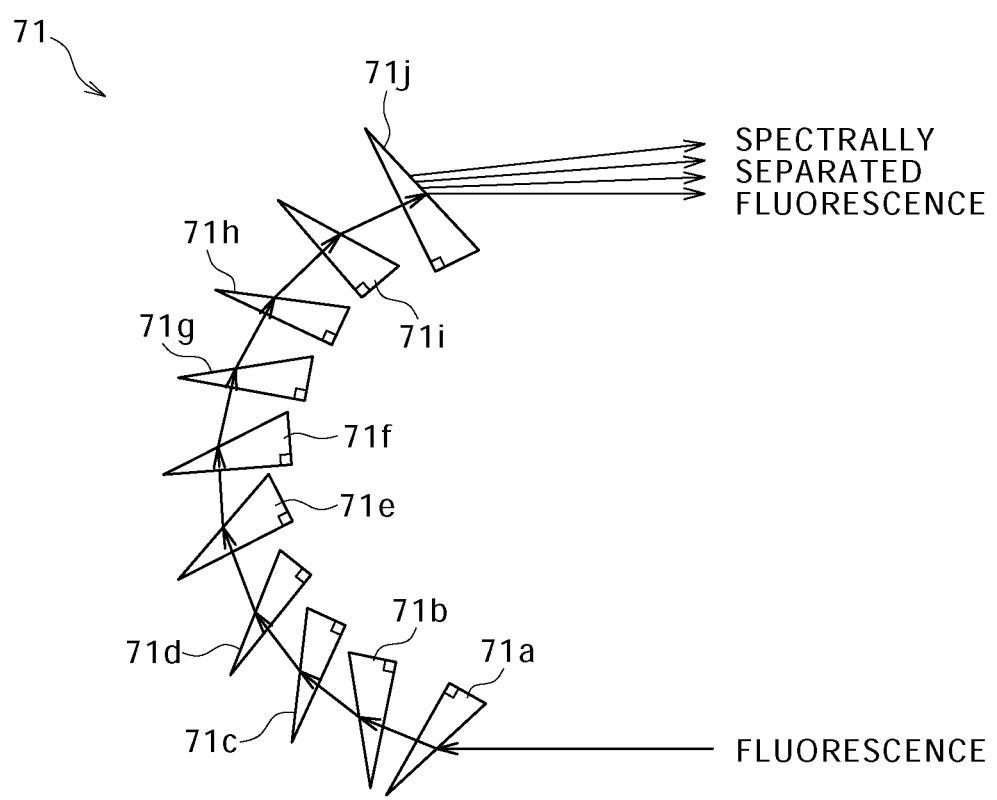
FIG. 15 is a schematic diagram showing the configuration of a light separator shown in FIG. 14.

FIG. 15 is a schematic diagram showing the configuration of the light separator 71 shown in FIG. 14. As shown in FIGS. 14 and 15, the light separator 71 in the optical measuring device 70 is composed of a plurality of prisms 71a to 71j arranged continuously. Each of the prisms 71a to 71j has at least two plane faces (incident surface and emergent surface) not parallel to each other, wherein the polarization dependence is smaller than that of a diffraction grating and unpolarized light can be separated efficiently.

In contrast, the polarization dependence of a diffraction grating is high. Accordingly, the fluorescence 6 must be once separated into orthogonal polarized components, and an optimum angle of deflection must be given to each polarized component with a maximum diffraction efficiency for the purposes of realization of highly efficient light separation. To give an optimum angle of deflection to each polarized component, an optical system is demanded. By using the prisms 71a to 71j as the light separator 71, high-precision measurement can be made with a smaller space and a smaller number of parts as compared with the case of using a diffraction grating. Accordingly, the optical measuring device can be further reduced in size and cost.

Preferably, the prisms 71a to 71j include a prism having a positive temperature coefficient of refractive index and a prism having a negative temperature coefficient of refractive index. A diffraction grating thermally expands or contracts according to temperature to cause a change in diffraction angle. To the contrary, the light separator 71 in the optical measuring device 70 according to this embodiment is composed of prisms formed of a glass material having a positive temperature coefficient of refractive index and prisms formed of a glass material having a negative temperature coefficient of refractive index. Accordingly, the temperature dependence of diffraction angle can be reduced. For example, the light separator 71 may be provided by the combination of prisms formed of a glass material S-NBH53 having a positive temperature coefficient of refractive index and prisms formed of a glass material S-HPH1 having a negative temperature coefficient of refractive index.

The light separator 71 in the optical measuring device 70 essentially includes at least one prism having a positive temperature coefficient of refractive index and at least one prism having a negative temperature coefficient of refractive index. However, by increasing the number of prisms in the light separator 71, the difference in diffraction angle between wavelengths can be enlarged. However, if the number of prisms is excessively increased, the transmittance of the light separator 71 is reduced. Accordingly, the number of prisms in the light separator 71 is preferably set to about ten.

Even in the case that the ten prisms 71a to 71j are used as the light separator 71 in the optical measuring device 70 as shown in FIG. 15, a transmittance of 90% or more can be easily attained by setting the supported wavelength to 500 to 800 nm. That is, a technique for forming an antireflection coating has already been established. Accordingly, by setting the wavelength bandwidth to 300 nm, which is the same as the standard bandwidth of an optical device for visible light, a transmittance of 90% or more can be obtained without the need of any special techniques. Further, in this supported wavelength, the glass material for the prisms 71a to 71j can be easily selected so that the total transmittance of the ten prisms becomes 90% or more. (Telecentric condenser lens 79)

The telecentric condenser lens 79 is an optical component for making parallel the optical axes of the plural light beams (diffracted light) separated by the light separator 71 and directing these parallel light beams toward the plural detection channels of the multichannel PMT 49. More specifically, the fluorescence 6 separated by the prisms 71a to 71j is condensed through the telecentric condenser lens 79 toward the plural detection channels of the multichannel PMT 49, thus forming an image on an image surface near the detection surface of each detection channel.

The telecentric condenser lens 79 is provided between the light separator 71 (the prisms 71a to 71j) and the multichannel PMT 49, so that the separated light beams from the light separator 71 can be efficiently condensed toward the plural detection channels of the multichannel PMT 49 without providing a plurality of optical components.

Preferably, the telecentric condenser lens 79 according to the optical measuring device 70 of the embodiment has a transmittance of 90% or more to the light having a wavelength range of at least 500 to 800 nm. Accordingly, optical loss in the telecentric condenser lens 79 can be suppressed to improve the detection efficiency in the multichannel PMT 49. The telecentric condenser lens 79 may be realized by combining a plurality of lenses having different characteristics.

Figure 16:
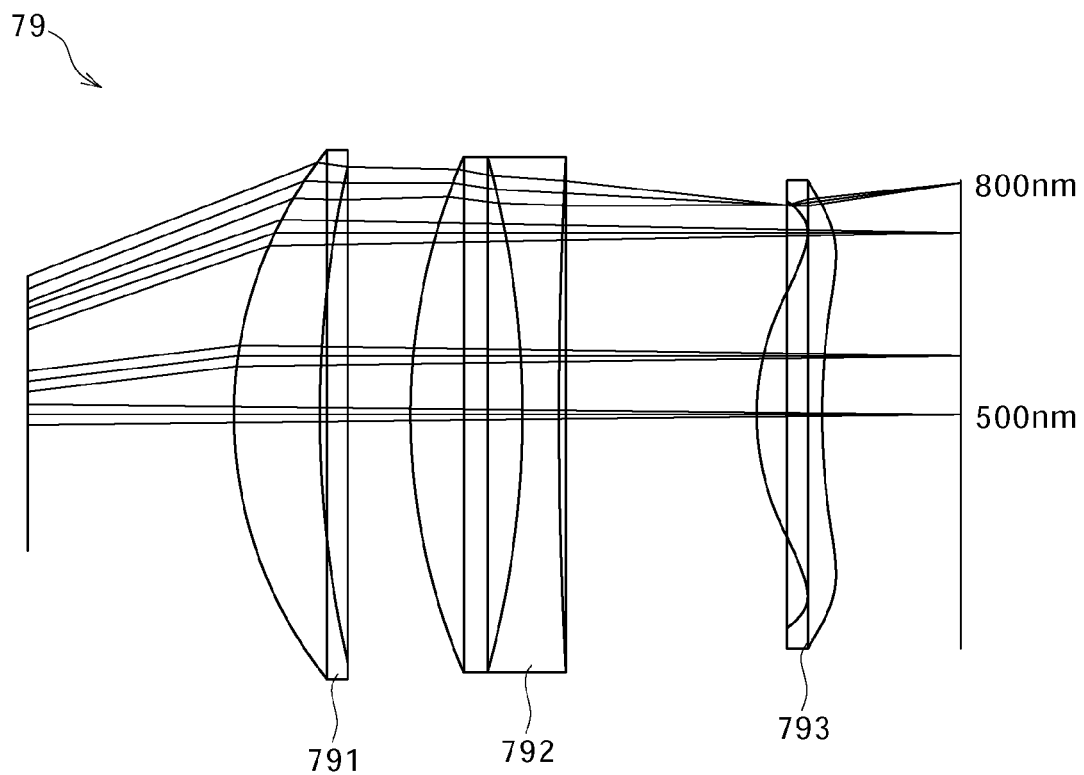
FIG. 16 is a schematic diagram showing the configuration of a telecentric condenser lens shown in FIG. 14.

FIG. 16 is a schematic diagram showing the configuration of the telecentric condenser lens 79 shown in FIG. 14. In the case that prisms are used as the light separator 71, the linearity between the wavelengths of the separated light beams and the diffraction angles thereof is reduced as compared with the case of using a diffraction grating. To cope with this problem, when the prisms 71a to 71j are used as the light separator 71, the telecentric condenser lens 79 preferably includes at least one aspherical lens 793 as shown in FIG. 16, so that a reduction in the linearity can be suppressed.

Further, the telecentric condenser lens 79 preferably includes at least one mirror, so that the condensing optical system can be folded to be reduced in size. As a modification, the telecentric condenser lens 79 may be replaced by a curved reflection mirror. Since a mirror has no wavelength dependence of reflection angle, a condensing optical system with reduced chromatic aberration can be obtained.

The telecentric condenser lens 79 is preferably configured by two or more lens groups symmetrical with respect to an axis. With this configuration, the diffraction angle linearity can be improved. Further, even when the image height in the multichannel PMT 49 is 0 to 32 mm, the maximum inclination angle of a principal ray with respect to the optical axis (telecentric characteristic) can be reduced to 10° or less in all field angles. Further, in the case that the telecentric condenser lens 79 is configured by four lenses of three groups including an aspherical lens, the telecentric characteristic can be reduced to 6.5° or less and the RMS spot diameter of all the separated light beams can be reduced to 100 μm or less in the case that the image height is 0 to 32 mm.

In the case that the effective detection width on the detection surface of the multichannel PMT 49 is 70% of the pitch of the detection channels, the total quantity of photons reaching the detection channels is less than 70%. Further, in the case that the light quantity of the fluorescence 6 is small, the S/N is reduced by shot noise. In the optical measuring device 70, however, a microlens array 50 is provided just before the detection surface of the multichannel PMT 49, so that all of the light beams from the telecentric condenser lens 79 can be guided to enter the respective detection channels as avoiding the dead zones.

In the case that the telecentric characteristic of the incident light (the fluorescence 6) is reduced to 10° or less by the telecentric condenser lens 79, all of the light beams can reach the detection channels of the multichannel PMT 49. Further, in the case that the telecentric characteristic of the incident light (the fluorescence 6) is reduced to 6.5° or less by the telecentric condenser lens 79, all of the light beams can reach the detection channels including a production margin. As a result, it is possible to enhance the effect of improving the efficiency of incidence of light to each detection channel of the multichannel PMT 49 by the microlens array 50, thereby further improving the detectivity in the multichannel PMT 49.

With the above-mentioned configuration of the telecentric condenser lens 79, the diffraction angle linearity can also be improved about 30%. This rate of improvement in the linearity means the rate of correction of an image forming position at a diffraction angle corresponding to an arbitrary wavelength within the wavelength bandwidth of a detectable wavelength band (e.g., 500 to 800 nm) toward an ideal image forming position in the case that a deviation in image forming position between the opposite ends of the detactable wavelength band is 32 mm and that the image forming position is ideally linearly interpolated.

Objective Lens 72

The objective lens 72 functions to trap the fluorescence 6 generated from the sample. Preferably, the objective lens 72 has a numerical aperture NA and a transmittance such that the product of the square of the numerical aperture NA and the transmittance is 0.5 or more in the wavelength range of at least 500 to 800 nm, and the objective lens 72 is configured by two or more lens groups including an aspherical lens. With this configuration, the fluorescence 6 generated from the sample can be trapped at a sufficient coupling rate and can be sent toward the detector (the multichannel PMT 49).

An objective lens has a property such that when the numerical aperture NA is increased, the light quantity trapping efficiency is increased twice the numerical aperture NA, but the focal depth is decreased with the square of the numerical aperture NA. Accordingly, when the numerical aperture NA is increased in a system where object points are unstable as in a flow cytometry device or a beads assay device, image forming characteristics are deteriorated. For example, in the case of an objective lens having a numerical aperture NA of 0.85 and a transmittance of 73%, the product of the square of the numerical aperture NA and the transmittance becomes 0.527, which is greater than 0.5, so that a sufficient quantity of transmitted light can be obtained, but the focal depth is lacking.

This index (the product of the square of the numerical aperture NA and the transmittance) is proportional to the light quantity trapping efficiency. Accordingly, when using an objective lens having a transmittance of 95% and a numerical aperture NA of 0.75, it is possible to obtain a light quantity trapping efficiency similar to that obtained by using the above objective lens having a numerical aperture NA of 0.85. When the numerical aperture NA is 0.75, the focal depth is increased about 30% as compared with the case that the numerical aperture NA is 0.85. Accordingly, an optical margin can be widened and low-cost lens design can be made in such a manner that the objective lens is configured by two lens groups including an aspherical molded lens.

Pinhole 77

The pinhole 77 functions to remove noise derived from fluorescence generated from any matter other than the sample in a confocal optical system. The pinhole 77 may be provided by a circular pinhole having an inverted projection size of about 40 μm in diameter to a target area to be measured. That is, when the projection magnification from the target area to be measured to the pinhole 77 is 10 times, the pinhole 77 has a pinhole diameter of 400 μm. Even when samples are continuously detected, signals derived from these samples can be easily separated by narrowing the field of view to an object.

(Filter 76)

When the laser light 5 is applied to the sample, a fluorochrome included in the sample is excited to generate the fluorescence 6. At this time, scattering of the exciting light also occurs and this scattered light is also trapped together with the fluorescence 6 by the objective lens 72. In the optical measuring device 70, the filter 76 is located just before the pinhole 77 to remove the above-mentioned scattered light. The filter 76 may be provided by a band-cut filter for reflecting light having a specific wavelength. Accordingly, also in the case that a plurality of laser beams having different wavelengths are applied, each laser spot is projected just before the pinhole 77, so that the scattered light can be efficiently removed by the filter 76.

Operation of the Optical Measuring Device 70

There will now be described the operation of the optical measuring device 70, i.e., a method of optically measuring a sample such as cells or microbeads by using the optical measuring device 70. The sample to be measured by the optical measuring device 70 may be modified by one or more fluorochromes.

In the optical measuring device 70, a sample is allowed to flow in the channel formed in the channel chip 2, and the laser light 5 emitted from the laser light source 31 in the light applying section 3 is condensed by the objective lens 36 and applied to the sample. A semiconductor laser (LD) having a center wavelength of 488 nm may be used as the laser light source (exciting laser source) 31. A semiconductor laser has a property such that its emission wavelength is shifted according to variations between lots, oscillation power, and temperature. However, even when the wavelength of the laser light 5 is shifted by about 5 nm from the excitation spectral peak wavelength of the fluorochrome, a large change does not arise in the light quantity of the fluorescence 6.

The fluorescence 6 generated from the sample is trapped by the objective lens 72 in the fluorescence detecting section 18, and is next condensed by the condenser lens 74. The fluorescence 6 thus condensed is reflected by the mirror 75 to enter the filter 76. Then, any disturbance components other than the fluorescence 6 generated from the sample are removed by the filter 76 and the pinhole 77. Thereafter, the fluorescence 6 passed through the pinhole 77 is converted into a parallel light beam by the collimator lens 78, and next separated according to wavelengths by the prisms 71a to 71j. The light beams separated by the prisms 71a to 71j are condensed by the telecentric condenser lens 79 to enter the respective detection channels of the multichannel PMT 49.

While the single laser light source 31 is provided in the light applying section 3 of the optical measuring device 70 shown in FIG. 14, the present embodiment is not limited to this configuration, but a plurality of light sources having different emission wavelengths may be provided in the light applying section 3. In this case, at least one of the plural light sources preferably emits laser light having a center wavelength of 488 nm. In the case that a plurality of light sources are provided in the light applying section 3, the fluorescence detecting section 18 may include an optical system for separating a plurality of fluorescence beams derived from the plural laser beams emitted from the plural light sources and efficiently detecting the plural separated fluorescence beams.

As described above, the prisms 71a to 71j are used as the light separator 71 in the optical measuring device 70 according to this embodiment. Accordingly, high-precision measurement can be made with a smaller space and a smaller number of parts as compared with the case of using a diffraction grating. As a result, although the multichannel PMT 49 is used as the detector in this embodiment, the fluorescence 6 generated from the sample can be detected with high sensitivity. Further, the optical measuring device can be further reduced in size.

The other configuration and effect in the optical measuring device 70 are similar to those of the first to third embodiments. Further, as in the fifth embodiment, a scattered light detecting section may be provided in addition to the fluorescence detecting section 18 in the optical measuring device 70. Also in this case, similar effects can be obtained.

EXAMPLES

The effect of the present embodiment will now be described more specifically in comparison with an existing optical measuring device. In Examples, the optical measuring device 12 according to the fourth embodiment shown in FIG. 10 (Example 1) and the optical measuring device 70 according to the sixth embodiment shown in FIG. 14 (Example 2) were compared with the existing optical measuring device in terms of detection efficiency.

The objective lens 41 used in the optical measuring device according to the Example 1 was a lens having a focal length of 8 mm, a field diameter of 150 μm, a numerical aperture NA of 0.8, and a transmittance of 90% or more to the light having a wavelength range of 400 to 800 nm. The slit 52 used in the optical measuring device according to the present embodiment was a rectangular slit having an opening length 1 of 1.5 mm and an opening width w of 0.4 mm. The focal length of the condenser lens for the slit 52 was set to 80 mm, and the slit 52 was located in confocal relationship with the objective lens 41.

Further, the longitudinal direction of the rectangular slit 52 was set in parallel relationship with the flowing direction of the sample. The polarization beam splitter 45 used in the optical measuring device according to the present embodiment was a wide-band polarization beam splitter capable of supporting the light having a wavelength range of 500 to 800 nm. The incident light to the polarization beam splitter 45 was separated into P-polarized light and S-polarized light, and the P-polarized light was passed twice continuously through the Fresnel rhomb 53 having an inclined surface inclined 45° with respect to a polarization plane, thereby 90° rotating the polarization direction of the P-polarized light. The two light beams having the polarization direction of the S-polarized light from the polarization beam splitter 45 and the Fresnel rhomb 53 were directed to the transmission gratings 47a and 47b having rectangular grooves to thereby obtain two layers of sectorially diverging spectral light, which are next imaged by the single telecentric condenser lens 48 corrected in chromatic aberration.

The objective lens 72 used in the optical measuring device 70 as Example 2 was a lens having a focal length of 4 mm, a field diameter of 150 μm, a numerical aperture NA of 0.75, and a transmittance of 90% or more to the light having a wavelength range of 400 to 800 nm. The pinhole 77 used in the optical measuring device 70 as Example 2 was a pinhole having a pinhole diameter of 1.2 mm. The focal length of the condenser lens 74 for the pinhole 77 was set to 120 mm, and the pinhole 77 is located in confocal relationship with the objective lens 72. Further, different glass materials P1 and P2 shown below in Table 1 were used for the prisms 71a to 71j. More specifically, the glass material P1 was used for the six prisms 71a, 71c, 71d, 71g, 71h, and 71j, whereas the glass material P2 was used for the four prisms 71b, 71e, 71f, and 71i.

TABLE 1

|  |  | P1 | P2 |
|---|---|---|---|
| Glass material type | | S-NBH53 | S-NPH1 |
| Prism angle (degrees) | | 16.9 | 20.6 |
| Temperature coefficient of refractive index [temperature range: 20 to 40° C.] dn/dt ($10^{-6}$/° C.) | F' line (488.0 nm) | 6.7 | 2.1 |
| | E line (546.1 nm) | 5.8 | 0.4 |
| | D line (587.6 nm) | 5.5 | −0.3 |
| | C line (643.9 nm) | 5.1 | −0.8 |
| Number of prisms | | 6 | 4 |

The multichannel PMT 49 used both in the optical measuring device 12 as Example 1 and in the optical measuring device 70 as Example 2 was a 32-channel multiarray PMT whose photoelectric surface has a maximum quantum efficiency of 25% at a wavelength of 490 nm. Further, the microlens array 50 located just before the detection surface of the multichannel PMT 49 was a microlens array having a plurality of cylindrical lenses arranged with a pitch of 1 mm which is the same as the pitch of the detection channels of the PMT 49. The focal points of the telecentric condenser lens was set at the joints of the cylindrical lenses of the microlens array 50.

The performance of the optical measuring device according to the Examples 1 and 2 in comparison with the existing optical measuring device is shown in

TABLE 2

|  | Comparison | Embodiment 1 | | Embodiment 2 | |
|---|---|---|---|---|---|
|  | (Existing art) | Performance | Efficiency | Performance | Efficiency |
| Numerical aperture NA of objective lens | 0.4 | 0.8 | x4 | 0.75 | x3.5 |
| Maximum quantum efficiency of PMT | 18% | 25% | x1.5 | 25% | x1.5 |
| Transmittance (Objective lens) (Diffraction grating - PMT) | 20 to 44% (53 to 65%) (37 to 68%) | 40 to 74% (80 to 94%) (50 to 79%) | x2 | 76 to 82% (95 to 97%) (80 to 85%) | x2 to 3 |
| Photon trap efficiency of PMT | 60% | 100% | x1.5 | 100% | x1.5 |
| Total efficiency | — | — | x18 | — | x16 to 24 |

As apparent from Table 2, it was confirmed that the fluorescence detection efficiency in the optical measuring device according to the present embodiment is improved as compared with the existing optical measuring device.

It should be understood that various changes and modifications to the presently embodiments described herein will be apparent to those skilled in the art. Such changes and modifications can be made without departing from the spirit and scope and without diminishing its intended advantages. It is therefore intended that such changes and modifications be covered by the appended claims.

The application is claimed as follows:

1. A flow cytometer comprising:
    a light applying section configured to apply laser light to a sample flowing in a channel; and
    a fluorescence detecting section configured to detect fluorescence generated from said sample irradiated with said laser light;
    said fluorescence detecting section including
    a multichannel photomultiplier tube having a plurality of detection channels capable of simultaneously detecting a plurality of light beams generated by the sample,
    a light separator configured to separate said fluorescence according to wavelengths to provide said plurality of light beams generated by the sample, said light separator being provided by a transmission grating or a prism, and
    a telecentric condenser lens configured to receive said plurality of light beams generated by the sample from said light separator and direct said plurality of light beams toward said plurality of detection channels of said multichannel photomultiplier tube so that the optical axes of said plurality of light beams are parallel to each other.

2. The flow cytometer according to claim 1, wherein said telecentric condenser lens is configured by combining a plurality of lenses different in characteristics, and has a transmittance of 90% or more to the light having a wavelength range of 500 to 800 nm.

3. The flow cytometer according to claim 2, wherein said light separator is provided by said prism, and said telecentric condenser lens includes an aspherical lens.

4. The flow cytometer according to claim 1, wherein said light separator includes at least one prism having a positive temperature coefficient of refractive index and at least one prism having a negative temperature coefficient of refractive index.

5. The flow cytometer according to claim 1, wherein
    said fluorescence detecting section further includes a microlens array provided between said telecentric condenser lens and said multichannel photomultiplier tube; and
    said plurality of light beams emerged from said telecentric condenser lens are passed through said microlens array to enter said plurality of detection channels of said multichannel photomultiplier tube.

6. The flow cytometer according to claim 5, wherein
said microlens array is composed of a plurality of cylindrical lens arranged so that the axes of said cylindrical lenses are parallel to each other, the number of said cylindrical lenses corresponding to the number of said detection channels of said multichannel photomultiplier tube; and
the direction of arrangement of said cylindrical lens coincides with the direction of arrangement of said detection channels of said multichannel photomultiplier tube.

7. The flow cytometer according to claim 1, wherein
said fluorescence detecting section further includes an objective lens configured to condense said fluorescence generated from said sample; and
said objective lens is configured by combining a plurality of lenses different in characteristics, and has a focal length of 8 mm or more, a numerical aperture NA of 0.8 or more, and a field diameter of 150 μm or more.

8. The flow cytometer according to claim 7, wherein
said fluorescence detecting section further includes a rectangular slit provided between said objective lens and said light separator, said rectangular slit having a length of 0.2 to 1.5 mm and a width of 0.4 mm or less; and
said slit is arranged so that the longitudinal direction of said slit is parallel to the flowing direction of said sample.

9. The flow cytometer according to claim 7, wherein said fluorescence detecting section further comprises a pinhole provided between said objective lens and said light separator.

10. The flow cytometer according to claim 7, wherein said fluorescence detecting section further includes a polarization beam splitter and a Fresnel rhomb provided between said objective lens and said light separator;
said polarization beam splitter being capable of separating the light having a wavelength range of 500 to 800 nm into a parallel polarized light component and an orthogonal polarized light component;
said Fresnel rhomb being capable of 90° rotating the polarization direction of one of said parallel polarized light component and said orthogonal polarized light component separated by said polarization beam splitter.

11. A flow cytometer comprising:
light applying means for applying laser light to a sample flowing in a channel; and
fluorescence detecting means for detecting fluorescence generated from said sample irradiated with said laser light;
said fluorescence detecting means including
a multichannel photomultiplier tube having a plurality of detection channels capable of simultaneously detecting a plurality of light beams generated by the sample,
a light separator for separating said fluorescence according to wavelengths to provide said plurality of light beams generated by the sample, said light separator being provided by a transmission grating or a prism, and
a telecentric condenser lens for receiving said plurality of light beams generated by the sample from said light separator and directing said plurality of light beams toward said plurality of detection channels of said multichannel photomultiplier tube so that the optical axes of said plurality of light beams are parallel to each other.

12. The flow cytometer according to claim 1, wherein the telecentric condenser lens directs said plurality of light beams toward said plurality of detection channels of said multichannel photomultiplier tube without a plurality of optical elements provided to condense the plurality of light beams on each of the plurality of detection channels.

* * * * *